(12) United States Patent
Adu-Bobie et al.

(10) Patent No.: US 10,336,794 B2
(45) Date of Patent: Jul. 2, 2019

(54) IMMUNOGENIC BACTERIAL VESICLES WITH OUTER MEMBRANE PROTEINS

(71) Applicant: GLAXOSMITHKLINE BIOLOGICALS SA, Rixensart (BE)

(72) Inventors: Jeannette Adu-Bobie, Siena (IT); Mariagrazia Pizza, Siena (IT); Nathalie Norais, Siena (IT); Germano Ferrari, Ghedi (IT); Guido Grandi, Siena (IT)

(73) Assignee: GLAXOSMITHKLINE BIOLOGICALS S.A. (BE)

( * ) Notice: Subject to any disclaimer, the term of this patent is extended or adjusted under 35 U.S.C. 154(b) by 0 days.

(21) Appl. No.: 15/698,434

(22) Filed: Sep. 7, 2017

(65) Prior Publication Data
US 2018/0009852 A1 Jan. 11, 2018

Related U.S. Application Data

(62) Division of application No. 14/927,052, filed on Oct. 29, 2015, now Pat. No. 9,771,399, which is a division of application No. 11/666,786, filed as application No. PCT/IB2005/003494 on Oct. 28, 2005, now Pat. No. 9,206,399.

(30) Foreign Application Priority Data

Oct. 29, 2004 (GB) .................................. 0424092.5

(51) Int. Cl.

| | | |
|---|---|---|
| A61K 39/02 | (2006.01) | |
| C07K 14/22 | (2006.01) | |
| C07K 14/245 | (2006.01) | |
| A61K 39/095 | (2006.01) | |
| C12N 9/10 | (2006.01) | |
| A61K 39/108 | (2006.01) | |
| A61K 39/00 | (2006.01) | |

(52) U.S. Cl.
CPC .......... *C07K 14/245* (2013.01); *A61K 39/095* (2013.01); *C07K 14/22* (2013.01); *C12N 9/1051* (2013.01); *A61K 39/00* (2013.01); *A61K 39/0258* (2013.01); *Y02A 50/474* (2018.01)

(58) Field of Classification Search
None
See application file for complete search history.

(56) References Cited

U.S. PATENT DOCUMENTS

| | | | |
|---|---|---|---|
| 6,180,111 B1 | 1/2001 | Stein et al. | |
| 6,355,253 B1 | 3/2002 | Zlotnick | |
| 6,451,317 B1 | 9/2002 | Milan et al. | |
| 6,936,261 B2 * | 8/2005 | Granoff .................. | A61K 31/56 424/234.1 |
| 7,018,636 B1 | 3/2006 | Bhattacharjee et al. | |
| 7,384,645 B2 | 6/2008 | Foster et al. | |
| 7,628,995 B2 | 12/2009 | Bos et al. | |
| 7,754,218 B2 | 7/2010 | Contorni et al. | |
| 7,838,014 B2 | 11/2010 | Biemans et al. | |
| 8,007,815 B1 | 8/2011 | Granoff et al. | |
| 8,029,807 B2 | 10/2011 | Bos et al. | |
| 8,663,656 B2 | 3/2014 | Pizza | |
| 8,808,711 B2 | 8/2014 | Oster et al. | |
| RE45,137 E | 9/2014 | O'Hagan et al. | |
| 8,968,748 B2 | 3/2015 | Granoff et al. | |
| 9,206,399 B2 * | 12/2015 | Adu-Bobie .......... | A61K 39/095 |
| 2004/0116665 A1 | 6/2004 | Berthet et al. | |
| 2006/0029621 A1 | 2/2006 | Granoff et al. | |
| 2006/0240045 A1 | 10/2006 | Berthet et al. | |
| 2007/0059329 A1 | 3/2007 | Norals et al. | |
| 2011/0182942 A1 | 7/2011 | Zollinger | |
| 2011/0262484 A1 | 10/2011 | Feavers | |
| 2016/0108094 A1 | 4/2016 | Adu-Bobie et al. | |

FOREIGN PATENT DOCUMENTS

| | | |
|---|---|---|
| EP | 0011243 B1 | 4/1982 |
| EP | 1741443 B1 | 10/2007 |
| WO | WO-99/61053 A1 | 12/1999 |
| WO | WO-01/34642 A2 | 5/2001 |
| WO | WO-01/91788 A1 | 12/2001 |
| WO | WO-02/09643 A2 | 2/2002 |
| WO | WO-02/062378 A | 8/2002 |
| WO | WO-2004/019977 A2 | 3/2004 |
| WO | WO-04/054611 A1 | 7/2004 |
| WO | WO-2005/004908 A1 | 1/2005 |
| WO | WO-2005/064021 A2 | 7/2005 |
| WO | WO-2006/046143 A2 | 5/2006 |
| WO | WO-2009/158142 A1 | 12/2009 |

OTHER PUBLICATIONS

Lommatzsch et al 1997 Journal of Bacteriology, p. 5465-5470.*
Templin et al 1992, JBC, vol. 267, No. 28, Issue of Oct. 5, pp. 20039-20043.*
"VA-MENGOC-BC," Product information from S.C.S. Farmacia Manes, Argentina. Cited in International Search Report for PCT/US99/11977 dated May 28, 1999. 1 page.
Adu-Bobie, J. et al. (2004) "GNA33 of Neisseria meningitidis is a lipoprotein required for cell separation, membrane architecture, and virulence" Infection and Immunity 72(4):1914-1919.
Arigita, C. at al. "Stability of mono- and trivalent meningococcal outer membrane vesicle vaccines," Vaccine, vol. 22, No. 5-0, 2004, pp. 630-643.

(Continued)

*Primary Examiner* — Padmavathi Baskar

(57) ABSTRACT

Knockout of the meningococcal mltA homolog gives bacteria that spontaneously release vesicles that are rich in immunogenic outer membrane proteins and that can elicit cross-protective antibody responses with higher bactericidal titres than OMVs prepared by normal production processes. Thus the invention provides a bacterium having a knockout mutation of its mltA gene. The invention also provides a bacterium, wherein the bacterium: (i) has a cell wall that includes peptidoglycan; and (ii) does not express a protein having the lytic transglycosylase activity MltA protein. The invention also provides compositions comprising vesicles that, during culture of bacteria of the invention, are released into the culture medium.

9 Claims, 10 Drawing Sheets

Specification includes a Sequence Listing.

(56) References Cited

OTHER PUBLICATIONS

Berlanda Scorza et al. (2008). "Proteomics characterization of outer membrane vesicles from the extraintestinal pathogenic *Escherichia coli* DeltatoIR IHE3034 mutant," Mol Cell Proteomics, 7(3):473-85.

Bernadac, A et al. (1998). "*Escherichia coli* tol-pal Mutants Form Outer Membrane Vesicles," Journal of Bacteriology, vol. 180, No. 18, pp. 4872-4878.

Bjune et al. (1991). "Effect of outer membrane vesicle vaccine against group B meningococcal disease in Norway," Lancet 338(8775):1093-1096.

Boslego J, et al. (1995). Efficacy, safety, and immunogenicity of a meningococcal group B (15:P1.3) outer membrane protein vaccine in Iquique, Chile. Chilean National Committee for Meningococcal Disease. Vaccine 13:821-829.

CECMED (Dec. 2, 2011), "Resumen de las Caracteristicas del Producto: VA-MENGOC-BC," Ministerio de Salud Publica de Cuba, 4 pages. (3 page English translation included).

Collins. (2011). "Gram-negative outer membrane vesicles in vaccine development," Discov Med, 12(62):7-15.

Corbel. (1994). "Control testing of combined vaccines: a consideration of potential problems and approaches," *Biologicals* 22(4):353-360.

Dalseg et al. (1999). "Outer membrane vesicles from group B meningococci are strongly immunogenic when given intranasally to mice" Vaccine 17(19):2336-2345.

De Kleijn, ED. et al. (2000). "Immunogenicity and safety of a hexavalent meningococcal outer membrane-vesicle vaccine in children of 2-3 and 7-8 years of age," Vaccine, 18:1456-1466.

De Moraes JC, et al. (1992). Protective efficacy of a serogroup B meningococcal vaccine in Sao Paulo, Brazil. Lancet 340: 1074-1078.

Debbag et al. (1994). "Evaluacion de las reacciones adversas asociadas con la vacuna antimeningococcica BC. Informe perliminar sobre 8,117 vacunados." Rev Hosp Ninos BAires, No. 158/159, 6 pages. (6 page English translation included).

Debbag et al. (1995). "Evaluation of Adverse Reactions Associated to Antimeningococcal BC Vaccination in 16,700 Children" Clinical Infectious Diseases, vol. 21, pp. 790-A420.

Decision revoking EP1644035, filed in Opposition against EP1644035, dated Jan. 20, 2014, 14 pages.

Declaration from Christiane Feron, filed in opposition against EP1534326, dated Sep. 28, 2009, 3 pages.

Devoe et al. (1973). "Release of endotoxin in the form of cell wall blebs during in vitro growth of Neisseria meningitidis," J Exp Med, 138(5):1156-67.

Ellis et al. (2010). "Virulence and immunomodulatory roles of bacterial outer membrane vesicles," Microbiol Mol Biol Rev, 74(1):81-94.

Experimental data regarding OMV expression following OMV extraction, filed in opposition against EP1534326, dated Oct. 2, 2009, 1 page.

Experimental data: expression of NspA, fHBP and GNA2132 in N. meningitidis, filed in opposition against EP1534326, dated Aug. 4, 2010. 2 pages.

Ferrari et al. (2006). "Outer membrane vesicles from group B Neisseria meningitidis delta gna33 mutant: proteomic and immunological comparison with detergent-derived outer membrane vesicles," Proteomics, 6(6):1856-66.

Frasch et al. (2001). "Outer Membrane Protein Vesicle Vaccines for Meningococcal Disease," Chapter 7 in "Methods in Molecular Medicine, Meningococcal Vaccines: Methods and Protocols," Pollard et al. (Ed), Humana Press, Totowa, New Jersey, vol. 66, pp. 81-107.

Fredrikson et al. (1991). "Production, characterization and control of MenB-vaccine Folkehelsa": an outer membrane vesicle vaccine against group B meningococcal disease. NIPH Annals 14:67-79.

Fukasawa et al. (1999) "Neisseria meningitidis serogroup C polysaccharide and serogroup B outer membrane vesicle conjugate as a bivalent meningococcus vaccine candidate." Vaccine 17:2951-2958.

Fukasawa et al. (2004). "Adjuvant can improve protection induced by OMV vaccine against Neisseria meningitidis serogroups B/C in neonatal mice" FEMS Immunol. Med. Microbiol. 41:205-210.

Galeano et al. (1995). "Efectividad de una vacuna antimeningococcica en una cohorte de itagui, Colombia, 1995," Epidemiologico de Antioquia 20(2), 8 pages. (9 page English translation included).

Gao et al. (1996). "Study on the LOS Antigenicity of 2 Candidate Strains for Meningococcal Vaccine of Serogroup B," Zhonghua Weishengwuxue He Mianyixue Zazhi 16(6):405-408. (English language Abstract only).

Gil et al. (2009). "Proteomic study via a non-gel based approach of meningococcal outer membrane vesicle vaccine obtained from strain CU385," Human Vaccines 5(5):347-356.

Henry, et al.(2004). "Improved methods for producing outer membrane vesicles in Gram-negative bacteria," Research in Microbiology, 155:437-446.

Hoiby et al. (1991). "Bactericidal antibodies after vaccination with the Norwegian meningococcal serogroup B outer membrane vesicle vaccine: a brief survey," NIPH Annals 14(2):147-155.

Hoiby et al. (1991). "The Norwegian meningococcal serogroup B outer membrane vesicle vaccine protection trials: case tracing, meningococcal antigen detection and serological diagnosis," NIPH Annals, 14(2):107-123.

Holst et al. (2003). "Serum bactericidal activity correlates with the vaccine efficacy of outer membrane vesicle vaccines against Neisseria meningitidis serogroup B disease," Vaccine 21(7-8):734-737.

Holst et al. (2009). "Properties and clinical performance of vaccines containing outer membrane vesicles from Neisseria meningitidis," Vaccine; 27 Suppl 2:B3-12.

Interlocutory decision in opposition proceedings, filed in opposition against EP1534326, dated Mar. 25, 2010, 11 pages.

International Preliminary Examination Report dated Aug. 23, 2000, for international patent application No. PCT/US99/11977, filed May 28, 1999, 7 pages.

Katial et al. (2002). "Immunogenicity and Safety Testing of a Group B Intranasal Meningococcal Native Outer Membrane Vesicle Vaccine," Infection and Immunity 70(2):702-707.

Koeberling et al. (2007). "Improved immunogenicity of a H44/76 group B outer membrane vesicle vaccine with over-expressed genome-derived Neisserial antigen 1870," Vaccine 25(10):1912-1920.

List of Journals from SpringerProtocols website about Methods in Molecular Biology, filed in Opposition against EP1644035, dated Oct. 18, 2014, 5 pages.

Lommatzsch et al. (1997). "Outer membrane localization of murine hydrolases: MltA, a third lipoprotein lytic transglycosylase in *Escherichia coli*," Journal of Bacteriology 179(17):5465-5470.

McLeod et al. (2000). "Structural relationships and sialylation among meningococcal L1, L8, and L3,7 lipooligosaccharide serotypes," J Biol Chem, 275(13):9716-24.

Milagres L G et al. (Aug. 2000) "Bactericidal antibody response to Neisseria meningitidis serogroup B in patients with bacterial meningitis: effect of immunization with an outer membrane protein vaccine," FEMS Immunology and Medical Microbiology 28(4):319-327.

Norheim et al. (2004). "Immunogenicity and bactericidal activity in mice of an outer membrane protein vesicle vaccine against Neisseria meningitidis serogroup A disease," Vaccine, 22: 2171-2180.

Norheim et al. (2005). "Development and characterisation of outer membrane vesicle vaccines against serogroup A Neisseria meningitidis" Vaccine 23(29):3762-3774.

Notice of Appeal by Carpmaels & Ransford, filed in Opposition against EP1644035, dated Mar. 24, 2014, 1 page.

Notice of Appeal by GlaxoSmithKline Biologicals S.A., filed in relation to EP1534326, dated Jun. 3, 2010, 2 pages.

Notice of opposition by GlaxoSmithKline Biologicals S.A., filed in opposition against EP1534326, dated Mar. 3, 2008, 19 pages.

Notice of Opposition, filed in Opposition against EP1644035, dated May 24, 2012, 15 pages.

(56) References Cited

OTHER PUBLICATIONS

O'Hallahan J, et al. 2004. The strategy to control New Zealand's epidemic of Group B meningococcal disease. PIDJ 23: S293-S298.
Ochoa, Rolando (2008). "Main projects on research, development and manufacturing of human vaccines," excerpt from presentation at BioQatar Symposium 2008, 4 slides.
Oster et al. (2007). "Immunogenicity and safety of a strain-specific MenB OMV vaccine delivered to under 5-year olds in New Zealand," Vaccine, 25:3075-9.
Parkhill et al. (2000). "Complete DNA Sequence of a Serogroup A Strain of Neisseria meningitides Z2491," Nature, 404(6777):502-506.
Patentee's response to Notice of Opposition, filed in Opposition against EP1644035, dated Mar. 12, 2013, 9 pages.
Patentee's response to opposition, filed in opposition against EP1534326, dated Jan. 19, 2009, 11 pages.
Peeters et al. (1996). "Phase I clinical trial with a hexavalent PorA containing meningococcal outer membrane vesicle vaccine," Vaccine 14(10):1009-1015.
Perez et al. (2010). "Community acquired bacterial meningitis in Cuba: a follow up of a decade," BMC Infectious Diseases 10:130, 9 pages.
Perkins et al. (1998). "Immunogenicity of two efficacious outer membrane protein-based serogroup B meningococcal vaccines among young adults in Iceland," *The Journal of Infectious Disease* 177:683-691.
Reply to Statement of Grounds of Appeal by Nederlandsch Octrooibureau, filed in Opposition against EP1644035, dated Oct. 15, 2014, 8 pages.
Rodriguez et al. (1999). "The epidemiological impact of antimeningococal B vaccination in Cuba," Mem Inst Oswaldo Cruz 94(4):433-440.
Rosenqvist et al. (1995). "Human Antibody Response to Meningococcal Outer Membrane Antigens after Three Doses of the Norwegian Group B Meningococcal Vaccine," Infection and Immunity 63(12):4642-4652.
Rosenqvist et al. (1998). "Effect of Aluminum Hydroxide and Meningococcal Serogroup C Capsular Polysaccharide on the Immunogenicity and Reactogenicity of a Group B Neisseria meningitidis Outer Membrane Vesicle Vaccine", Developments in Biological Standardization, vol. 92, pp. 323-333.
Sacchi et al. (2001). "Serosubtypes and PorA types of Neisseria meningitidis serogroup B isolated in Brazil during 1997-1998: overview and implications for vaccine development," J Clin Microbiol, 39(8):2897-903.
Sierra GV, et al. (1991). Vaccine against group B Neisseria meningitidis: protection trial and mass vaccination results in Cuba. NIPH Ann 14: 195-207.
Slide printout by Carpmaels & Ransford, filed in opposition against EP1534326, dated Nov. 23, 2009, 2 pages.
Statement of Grounds of Appeal by Carpmaels & Ransford, filed in Opposition against EP1644035, dated May 30, 2014, 5 pages.
Statement of Grounds of Appeal by GlaxoSmithKline Biologicals S.A., filed in relation to EP1534326, dated Aug. 4, 2010, 24 pages.
Tavano et al. (Jul. 2000). "The membrane expression of Neisseria meningitidis adhesin A (NadA) increases the proimmune effects of MenB OMVs on human macrophages, compared with NadA-OMVs, without further stimulating their proinflammatory activity on circulating monocytes," J Leukoc Biol 86(1):143-153.
Van de Waterbeemd (2012). "Identification and optimization of critical process parameters for the production of NOMV vaccine against Neisseria meningitidis," Vaccine, 30(24):3683-90.
Van der Ley & Steeghs. (2003). "Lessons from an LPS-deficient Neisseria meningitidis mutant" Journal of Endotoxin Research 9(2):124-128.
Van der Ley et al. (1992). "Construction of a Multivalent Meningococcal Vaccine Strain Based on the Class I Outer Membrane Protein," *Infection and Immunity* 60(8): 3516-3161.
Verheul et al. (1991). "Preparation, Characterization, and Immunogenicity of Meningococcal Immunotype L2 and L3,7,9 Phosphoethanolamine Group-Containing Oligosaccharide-Protein Conjugates," Infection and Immunity 59(3):843-851.
Vermont et al. (2003). "Meningococcal serogroup B infections: a search for a broadly protective vaccine," Expert Rev Vaccines, 2(5):673-81.
Wedege et al. (2003). "Antibody specificities and effect of meningococcal carriage in Icelandic teenagers receiving the Norwegian serogroup B outer membrane vesicle vaccine," Infect. Immun. 71:3775-3781.
Williams et al., (2007) "Proteomic analysis of outer membranes and vesicles from wild-type serogroup B Neisseria meningitidis and a lipopolysaccharide-deficient mutant" Infection and Immunity 75(3):1364-1372.
Wilson & Walker (Eds.) (1994). "Wilson Principles and techniques of practical biochemistry: Editors: Bryan L. Williams and Keith Wilson," Cambridge University Press, Cambridge, fourth edition, p. 309.
Written submission in preparation to oral proceedings by Carpmaels & Ransford, filed in Opposition against EP1644035, dated Oct. 18, 2013, 2 pages.
Written submission in preparation to oral proceedings by GlaxoSmithKline Biologicals S.A., filed in opposition against EP1534326, dated Sep. 30, 2009, 24 pages.
Written submission in preparation to oral proceedings by Nederlandsch Octrooibureau, filed in Opposition against EP1644035, dated Oct. 18 2013, 6 pages.
Zollinger et al. (2010). "Design and evaluation in mice of a broadly protective meningococcal group B native outer membrane vesicle vaccine," Vaccine, 28(31):5057-5067.
Tettelin et al., "Complete genome sequence of Neisseria meningitidis serogroup B strain MC58", 2000 Science 287 (5459): 1809-1815.

* cited by examiner

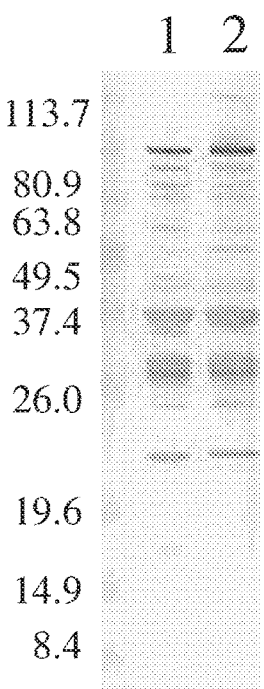
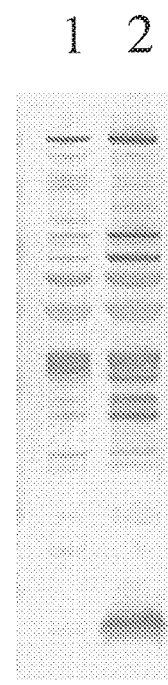
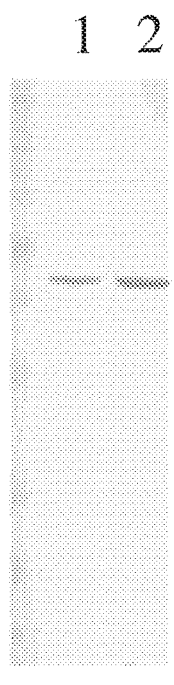
FIG. 4A  FIG. 4B  FIG. 4C
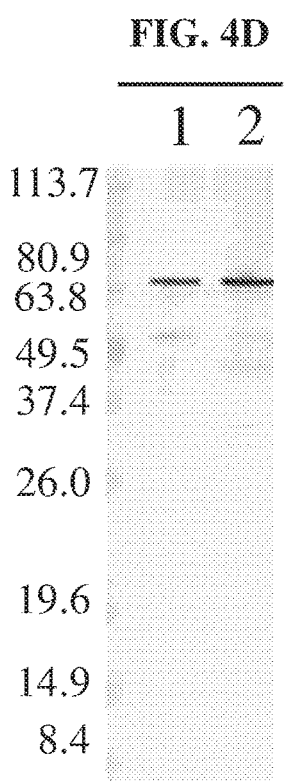
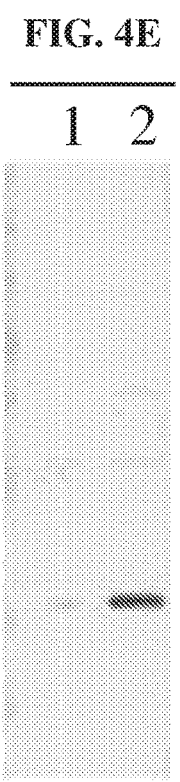
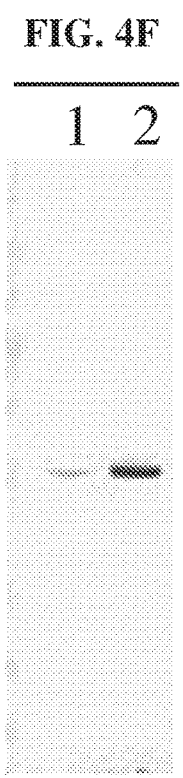
FIG. 4D  FIG. 4E  FIG. 4F FIG. 10A
FIG. 10B
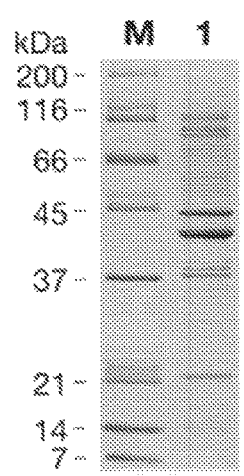
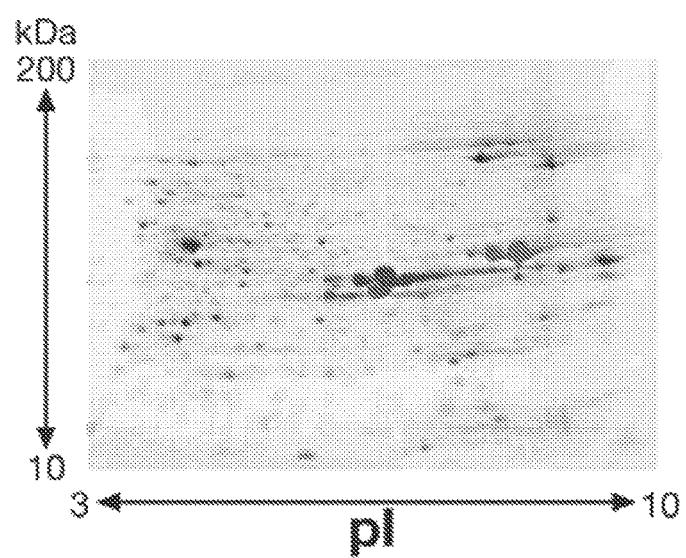

ated* and "GNA33" or "NMB0033" [26]) leads to the spontaneous
IMMUNOGENIC BACTERIAL VESICLES WITH OUTER MEMBRANE PROTEINS

SUBMISSION OF SEQUENCE LISTING AS ASCII TEXT FILE

The content of the electronically submitted sequence listing (Name: VN51982_Seq_Lstg.txt; Size 39,612,036 bytes; and Date of Creation: Aug. 28, 2017) was originally submitted in U.S. application Ser. No. 11/666,786 (now U.S. Pat. No. 9,206,399, filed Oct. 28, 2005) and is incorporated herein by reference in its entirety.

TECHNICAL FIELD

This invention is in the field of vesicle preparation for immunisation purposes.

BACKGROUND ART

One of the various approaches to immunising against *N.meningitidis* infection is to use outer membrane vesicles (OMVs). An efficacious OMV vaccine against serogroup B has been produced by the Norwegian National Institute of Public Health [e.g. ref. 1] but, although this vaccine is safe and prevents MenB disease, its efficacy is limited to the homologous strain used to make the vaccine.

The 'RIVM' vaccine is based on OMVs containing six different PorA subtypes. It has been shown to be immunogenic in children in phase II clinical trials [2].

Reference 3 discloses a vaccine against different pathogenic serotypes of serogroup B meningococcus based on OMVs which retain a protein complex of 65-kDa. Reference 4 discloses a vaccine comprising OMVs from genetically-engineered meningococcal strains, with the OMVs comprising at least one Class I outer-membrane protein (OMP) but not comprising a Class 2/3 OMP. Reference 5 discloses OMVs comprising OMPs which have mutations in their surface loops and OMVs comprising derivatives of meningococcal lipopolysaccharide (LPS).

As well as serogroup B *N.meningitidis*, vesicles have been prepared for other bacteria. Reference 6 discloses a process for preparing OMV-based vaccines for serogroup A meningococcus. References 7 and 8 disclose vesicles from *N.gonorrhoeae*. Reference 9 discloses vesicle preparations from *N.lactamica*. Vesicles have also been prepared from *Moraxella catarrhalis* [10, 11], *Shigella flexneri* [12, 13], *Pseudomonas aeruginosa* [12, 13], *Porphyromonas gingivals* [14], *Treponema pallidum* [15], *Haemophilus influenzae* [16 & 21] and *Helicobacter pylori* [17].

The failure of OMVs to elicit cross-protection against non-homologous strains is not well understood, particularly as most *N.meningitidis* isolates share a small number of conserved protective surface antigens that, if present in OMVs, would be expected to provide broad protective coverage. One possible explanation for the failure is the existence of variable immune-dominant surface antigens that prevent the conserved antigens from exerting their protective action, and the presence of immune-dominant hyper-variable proteins such as PorA has been extensively documented and demonstrated. Other possible explanations are that the methods for OMV preparation result in contamination with cytoplasmic and/or inner membrane proteins that dilute the protective outer membrane proteins, or that antigens are lost by the detergent extraction.

There have been various proposals to improve OMV efficacy. Reference 18 discloses compositions comprising OMVs supplemented with transferrin binding proteins (e.g. TbpA and TbpB) and/or Cn,Zn-superoxide dismutase. Reference 19 discloses compositions comprising OMVs supplemented by various proteins. Reference 20 discloses preparations of membrane vesicles obtained from *N.meningitidis* with a modified fur gene. Reference 21 teaches that nspA expression should be up-regulated with concomitant porA and cps knockout. Further knockout mutants of *N.meningitidis* for OMV production are disclosed in references 21 to 23. In contrast to these attempts to improve OMVs by changing expression patterns, reference 24 focuses on changing the methods for OMV preparation, and teaches that antigens such as NspA can be retained during vesicle extraction by avoiding the use of detergents such as deoxycholate.

It is an object of the invention to provide further and improved vesicle preparations, together with processes for their manufacture. In particular, it is an object of the invention to provide vesicles which retain important bacterial immunogenic components from *N.meningitidis*.

DISCLOSURE OF THE INVENTION

The invention is based on the surprising discovery that disruption of the pathways involved in degradation of peptidoglycan (the murein layer) gives bacteria that release vesicles into their culture medium, and that these vesicles are rich in immunogenic outer membrane proteins and can elicit broad-ranging bactericide immune responses. The vesicles are different from the OMVs that can be prepared by disrupting whole bacteria (e.g. by sonication and sarkosyl extraction [25]), and can be prepared without even disrupting bacterial cells e.g. simply by separating the vesicles from the bacteria by a process such as centrifugation.

In particular, the inventors have found that knockout of the meningococcal mltA homolog (also referred to as 'GNA33' or 'NMB0033' [26]) leads to the spontaneous release of vesicles that are rich in immunogenic outer membrane proteins and that can elicit broadly cross-protective antibody responses with higher bactericidal titres than OMVs prepared by normal production processes. This enhanced efficacy is surprising for two reasons: first, the NMB0033 protein has previously been reported to be highly effective in raising bactericidal antibodies (e.g. see table 1 of ref. 196) and to be a strong vaccine candidate (e.g. see table 2 of ref. 27), with a recommendation in reference 28 that it should be unregulated for vesicle production, so its loss would a priori be expected to reduce bactericidal efficacy rather than to increase it; second, the knockout strains do not have the correct topological organisation of the cellular membrane, and the main constituent proteins of normal OMVs (e.g. the PorA, PIB, class 4 and class 5 outer membrane proteins) had previously been reported to be released into culture medium [25]. The inventors have now found that the previously-reported release does not involve secretion of discrete proteins, but that instead the outer membrane proteins are released in the form of vesicles. These vesicles are advantageous over OMVs prepared by prior art means because they are released spontaneously into the culture medium and can thus be prepared simply and efficiently without the complicated and time-consuming disruption and purification methods that are normally used for preparing OMVs.

Thus the invention provides a bacterium having a knockout mutation of its mltA gene. The bacterium preferably also has a knockout mutation of at least one further gene e.g. the porA and/or porB and or lpxA genes.

The invention also provides a bacterium, wherein: (i) the bacterium has a cell wall that includes peptidoglycan; and (ii) the bacterium does not express a protein having the lytic transglycosylase activity of MltA protein. The bacterium is preferably a mutant bacterium i.e. the bacterium is a mutant strain of a wild-type species that expresses MltA protein. The bacterium preferably also does not express at least one further protein e.g. the PorA and/or PorB and/or LpxA proteins.

Preferred bacteria of the invention are in the genus Neisseria, such as N.meningitidis, and so the invention provides a meningococcus bacterium having a knockout mutation of its gna33 gene. A preferred meningococcus is gna33⁻ IpxA⁻ PorA⁻.

The invention also provides a composition comprising vesicles that, during culture of bacteria of the invention, are released into the culture medium. This composition preferably does not comprise any living and/or whole bacteria. This composition can be used for vaccine preparation.

The invention also provides a composition comprising vesicles, wherein the vesicles are present in the filtrate obtainable after filtration through a 0.22 μm filter of a culture medium in which a bacterium of the invention has been grown. This composition can be used for vaccine preparation.

The invention also provides a meningococcal vesicle, wherein the vesicle does not include at least one of (i.e. does not include 1, 2 or 3 of) MinD, FtsA, and/or phosphoenolpyruvate synthase. The invention also provides a meningococcal vesicle, wherein the vesicle does not include at least one of NMB proteins 0126, 0154, 0157, 0171, 0219, 0359, 0387, 0426, 0595, 0617, 0618, 0631, 0757, 0763, 0875, 0876, 0943, 0946, 0957, 1131, 1252, 1323, 1341, 1445, 1497, 1574, 1576, 1869, 1934, 1936, 2096 and/or 2101. The invention also provides a meningococcal vesicle, wherein the vesicle is substantially free from ribosomes. The invention also provides a meningococcal vesicle, wherein the vesicle is substantially free from any aminoacid-tRNA-synthetases. The invention also provides a meningococcal vesicle, wherein the vesicle is substantially free from any enzyme from the Krebs cycle. These vesicles will also not include MltA (because of the knockout mutation), but will include outer membrane proteins. The vesicles may include trimeric outer membrane proteins (FIG. 13).

The invention also provides a meningococcal vesicle, which includes the following 47 proteins: NMB0035, NMB0044, NMB0086, NMB0088, NMB0109, NMB0124, NMB0138, NMB0182, NMB0204, NMB0278, NMB0294, NMB0313, NMB0345, NMB0346, NMB0382, NMB0460, NMB0461, NMB0550, NMB0554, NMB0623, NMB0634, NMB0663, NMB0703, NMB0787, NMB0873, NMB0928, NMB1030, NMB1053, NMB1057, NMB1126, NMB1285, NMB1301, NMB1332, NMB1429, NMB1483, NMB1533, NMB1567, NMB1612, NMB1710, NMB1870, NMB1898, NMB1949, NMB1961, NMB1972, NMB1988, NMB2039 and NMB2091.

The invention also provides a meningococcal vesicle, which includes one or more (i.e. 1, 2, 3, 4, 5, 6, 7, 8, 9, 10, 11, 12, 13, 14, 15, 16, 17, 18, or 19) of the following 19 proteins: NMB0044, NMB0086, NMB0204, NMB0278, NMB0294, NMB0313, NMB0345, NMB0346, NMB0460, NMB0550, NMB0873, NMB0928, NMB1030, NMB1057, NMB1483, NMB1870, NMB1898, NMB1961, and/or NMB2091. See also Table 4 below.

The invention also provides a composition comprising a first set of vesicles of the invention and a second set of vesicles of the invention, wherein said first and second sets are prepared from different strains of meningococcus. The invention also provides a process for preparing a mixture of vesicles, comprising: (a) preparing vesicles of the invention from a first meningococcal strain; (b) preparing vesicles of the invention from a second meningococcal strain; and (c) combining the vesicles from (a) and (b). Combining vesicles from different strains can improve the coverage of clinical strains.

The invention also provides a process for preparing bacterial vesicles, comprising the steps of: (i) culturing a MltA⁻ bacterium in a culture medium such that the bacterium releases vesicles into said medium; and (ii) collecting the vesicles from said medium. The MltA⁻ bacterium is preferably a MltA knockout mutant. The vesicles can be collected by size separation (e.g. filtration, using a filter which allows the vesicles to pass through but which does not allow intact bacteria to pass through), which can conveniently be performed after centrifugation to preferentially pellet cells relative to the smaller vesicles (e.g. low speed centrifugation).

Peptidoglycan Metabolism

Peptidoglycan (also known as murein, mucopeptide or glycosaminopeptide) is a heteropolymer found in the cell wall of most bacteria. Peptidoglycan is the component that is primarily responsible for the mechanical strength of the bacterial cell wall and for maintaining cellular shape. In Gram-positive bacteria it is the major component of the cell wall. In Gram-negative bacteria it occurs as a layer between the cytoplasmic and outer membranes, and is covalently linked to the outer membrane via the Braun lipoprotein Peptidoglycan consists mainly of linear heteropolysaccharide backbone chains that are cross-linked by 'stem' peptides to form a lattice structure. It is a polymer so large that it can be thought of as a single immense covalently linked molecule. In E.coli the saccharide backbone is formed from alternating N-acetylglucosamine (GlcNAc) and N-acetylmuramic acid (MurNAc) residues. A MurNAc residue may be linked to a stem tetrapeptide. Cross-links between backbone chains are usually formed directly between D-alanine in one stem peptide and a meso-DAP of another. The E.coli structure is typical for Gram-negative bacteria, but there is more variation within Gram-positive bacteria e.g. in S.aureus 30-50% of the muramic acid residues are not acetylated, the stem peptide often has L-lysine in place of meso-DAP and isoglutamine in place of D-glutamate, and cross-links can occur between stem peptides.

The initial step in E.coli peptidoglycan biosynthesis is the formation of the UDP derivative of GlcNAc, which occurs in the cytoplasm. Some UDP-GlcNAc is converted to UDP-MurNAc in a reaction of UDP-GlcNAc and phosphoenolpyruvate (PEP), catalysed by PEP:UDP-GlcNAc enolpyruvyl transferase. Still within the cytoplasm, amino acids are added sequentially to UDP-MurNAc to form a UDP-MurNAc-pentapeptide known as the 'Park nucleotide' that includes a terminal D-alanyl-D-alanine. The Park nucleotide is then transferred to bactoprenol monophosphate in the cytoplasmic membrane, where UDP-GlcNAC is also added to make a bactoprenol-disaccharide-pentapeptide subunit. The disaccharide-pentapeptide subunit is then transferred into the periplasmic region, with bactoprenol-pyrophosphate remaining in the membrane. Within the periplasm the transferred subunit is inserted into a growing peptidoglycan.

To allow cell division, changes in shape, and import/export of large complexes (e.g. during conjugation) then peptidoglycan degradation must occur. In E.coli this degradation is caused by enzymes referred to as murein hydrolases [29], which as a family includes lytic transglycosylases (mltA, mltB, mltC, mltD, stl70, emtA), endopeptidases (pbp4, pbp7, mepA) and amidases (amiC). Muramidases such as lysozyme cleave the same β-(1-4)-glycosidic linkages between MurNAc and GlcNAc residues; unlike muramidases, however, the transglycosylases cleave the glycosidic bond with concomitant formation of 1,6-anhydromuramoyl residues (AnhMurNAc).

The standard peptidoglycan anabolic and catabolic pathways are thus well-characterised, as are the minor variations and modifications that occur between bacteria. The enzymes are well-characterised, and proteins have been readily annotated as being involved in the pathways when new bacterial genomic sequences have been published. The skilled person can thus easily determine the enzymes involved in the peptidoglycan metabolic pathway for any given bacterium, can easily identify the enzymes involved, and can easily identify the genes encoding those enzymes.

The invention is based on the knockout of the mltA gene, which encodes a membrane-bound lytic transglycosylase. The MltA family is recognised in INTERPRO (entry 'ipr005300') and PFAM (entry 'MltA' or 'PF03562'), and the PFAM record lists MltA proteins in bacteria as diverse as *Rhizobium loti*, *Bradyrhizobium japonicum*, *Brucella melitensis*, *Brucella suis*, *Rhizobium meliloti*, *Agrobacterium tumefaciens*, *Zymomonas mobilis*, *Caulobacter crescentus*, *Yersinia pestis*, *Salmonella typhimurium*, *Buchnera aphidicola*, *Photorhabdus luminescens*, *Escherichia coli*, *Shigella flexneri*, *Salmonella typhi*, *Pseudomonas aeruginosa*, *Pseudomonas putida*, *Pseudomonas syringae*, *Coxiella burnetii*, *Vibrio cholerae*, *Vibrio vulnificus*, *Vibrio parahaemolyticus*, *Haemophilus ducreyi*, *Pasteurella multocida*, *Chromobacterium violaceum*, *Neisseria meningitidis*, *Neisseria gonorrhoeae*, *Bordetella parapertussis*, *Bordetella bronchiseptica*, *Bordetella pertussis*, *Nitrosomonas europaea*, *Ralstonia solanacearum*, *Synechococcus elongatus*, *Gloeobacter violaceus*, and *Leptospira interrogans*.

Preferred bacteria for MltA knockout are in the *Neisseria* genus, with *N.meningitidis* being the most preferred bacterium. The MltA gene in serogroup B *N.meningitidis* has been referred to in the literature as 'GNA33' [25,26,196], and an example sequence has GenBank accession number 'AF226391.1'. The MltA gene in serogroup A ('NMA0279') has GenBank accession number NP_283118.1. Aligned polymorphic forms of meningococcal MltA can be seen in FIGS. 7 and 18 of reference 30. Two full genome sequences of *N.meningitidis* are available [31,32]. For any given strain of *N.meningitidis*, therefore, the skilled person will be able to identify the mltA gene. For meningococcus, the knocked-out mltA gene is preferably the gene which, in the wild-type strain, has the highest sequence identity to SEQ ID NO: 1 herein. MltA is a lipoprotein in meningococcus [26].

Knockout of mltA can result in reduced virulence, abnormal cell separation, abnormal cell morphology, undivided septa, double septa, cell clustering and sharing of outer membranes [25]. At the same time, however, the knockout mutation has surprisingly been found to give bacteria that can spontaneously produce vesicles that are immunogenic and enriched in outer membrane proteins.

Bacteria

The bacterium from which vesicles are prepared may be Gram-positive, but it is preferably Gram-negative. The bacterium may be from genus *Moraxella, Shigella, Pseudomonas, Treponema, Porphyromonas* or *Helicobacter* (see above for preferred species) but is preferably from the *Neisseria* genus. Preferred *Neisseria* species are *N.meningitidis* and *N.gonorrhoeae.*

Within *N.meningitidis*, any of serogroups A, C, W135 and Y may be used, but it is preferred to prepare vesicles from serogroup B. Where relevant, the meningococcus can be of any serotype (e.g. 1, 2a, 2b, 4, 14, 15, 16, etc.), of any serosubtype (P1.2; P1.4; P1.5; P1.5,2; P1.7,16; P1.7,16b; P1.9; P1.9,15; P1.12,13; P1.13; P1.14; P1.15; P1.21,16; P1.22,14; etc.) and of any immunotype (e.g. L1; L3,3,7; L10; etc.), and preferred bacteria include: B:4:P1.4; B:4:P1.15; B:15:P1.7,16. The meningococcus may be from any suitable lineage, including hyperinvasive and hypervirulent lineages e.g. any of the following seven hypervirulent lineages: subgroup I; subgroup III; subgroup IV-1; ET-5 complex; ET-37 complex; A4 cluster; lineage 3. These lineages have been defined by multilocus enzyme electrophoresis (MLEE), but multilocus sequence typing (MLST) has also been used to classify meningococci [ref. 33] e.g. the ET-37 complex is the ST-11 complex by MLST, the ET-5 complex is ST-32 (ET-5), lineage 3 is ST-41/44, etc.

Preferred strains within serogroup B are MC58, 2996, H4476 and 394/98. In some embodiments of the invention, however, the meningococcus is not strain MC58 and is not strain BZ232.

As well as having a knockout of mltA, the bacterium may have one or more knockout mutations of other gene(s). To reduce pyrogenic activity, for instance, the bacterium should have low endotoxin (LOS/LPS) levels, and this can be achieved by knockout of enzymes involved in LPS biosynthesis. Suitable mutant bacteria are already known e.g. mutant *Neisseria* [34,35] and mutant *Helicobacter* [36]. The IpxA mutant of meningococcus is preferred. Processes for preparing LPS-depleted outer membranes from Gram-negative bacteria are disclosed in reference 37.

In *N.meningitidis*, a preferred further knockout is the PorA class I outer membrane protein. Advantageously, such knockouts will not display the immunodominant hypervariable stain-specific PorA protein, thereby focusing a recipient's immune response on other antigens. In a specific aspect, the invention provides a *N.meningitidis* bacterium, comprising both a knockout mutation of MltA and a knockout mutation of PorA. The bacterium can also carry further knockout mutations e.g. in LOS/LPS synthetic pathways (e.g. IpxA), immunodominant variable proteins, PorB, OpA, OpC, etc.

As well as having knockouts of particular endogenous genes, the bacterium may express one or more genes that are not endogenous. For example, the invention may use a recombinant strain that expresses new genes relative to the corresponding wild-type strain. Although it is preferred to knockout PorA expression, in an alternative approach it is possible to engineer a meningococcus to express multiple PorA subtypes (e.g. 2, 3, 4, 5 or 6 of PorA subtypes: P1.7,16; P1.5,2; P1.19,15; P1.5c,10; P1.12,13; and P1.7h,4 [e.g. refs. 38, 39]). Expression of non-endogenous genes in this way can be achieved by various techniques e.g. chromosomal insertion (as used for introducing multiple PorA genes [40]), knockin mutations, expression from extra-chromosomal vectors (e.g. from plasmids), etc.

As well as down-regulating expression of specific proteins, the bacterium may over-express (relative to the corresponding wild-type strain) immunogens such as NspA, protein 287 [19], protein 741 [41], TbpA [18], TbpB [18], superoxide dismutase [18], etc.

The bacterium may also include one or more of the knockout and/or over-expression mutations disclosed in reference 16, 21-24 and/or 42-43. Preferred genes for downregulation and/or knockout include: (a) Cps, CtrA, CtrB, CtrC, CtrD, FrpB, GalB, HtrB/MsbB, LbpA, LbpB, LpxK, Opa, Opc, PilC, PorA, PorB, SiaA, SiaB, SiaC, SiaD, TbpA, and/or TbpB [16]; (b) CtrA, CtrB, CtrC, CtrD, FrpB, GalE, HtrB/MsbB, LbpA, LbpB, LpxK, Opa, Opc, PhoP, PilC, PmrE, PmrF, PorA, SiaA, SiaB, SiaC, SiaD, TbpA, and/or TbpB [21]; (c) ExbB, ExbD, rmpM, CtrA, CtrB, CtrD, GalB, LbpA, LpbB, Opa, Opc, PilC, PorA, PorB, SiaA, SiaB, SiaC, SiaD, TbpA, and/or TbpB [42]; and (d) CtrA, CtrB, CtrD, FrpB, OpA, OpC, PilC, PorA, PorB, SiaD, SynA, SynB, and/or SynC [43].

For meningococcal compositions, the selection criteria of reference 44 may be used.

Preferred vesicles are prepared from meningococci having one of the following subtypes: P1.2; P1.2,5; P1.4; P1.5; P1.5,2; P1.5,c, P1.5c,10; P1.7,16; P17,16b; P1.7h,4; P1.9; P1.15; P1.9,15; P1.12,13; P1.13; P1.14; P1.21,16; P1.22,14. The meningococcus is preferably in serogroup B.

Vesicles may also be prepared from the *Escherichia* genus, such as from the *E.coli* species. *E.coli* strains have traditionally been classified as either commensal or pathogenic, and pathogenic strains are then sub-classified as intestinal or extraintestinal strains. Classification may also be based on the 'K' antigens. The best-studied 'K' antigen is 'K1', which is considered to be the major determinant of virulence among those strains of *E.coli* that cause neonatal meningitis. Vesicles of the invention can be prepared from any of these *E.coli* strains, but are preferably from a pathogenic strain, including an extraintestinal pathogenic ('ExPBC' [45]) strain, a uropathogenic (UPEC) strain or a meningitis/sepsis-associated (MNBC) strains. Genome sequences of pathogenic strains are available in the databases under accession numbers AE005174, BA000007 and NC-004431. Rather than use a mltA knockout, it may be preferred to knockout one or more of the components of the *E.coli* Tol-Pal complex [46], such as tolA, tolQ, tolB, pal and/or tolR. Knockout of tolR is preferred. The meningococci do not have a homolog of the Tol-Pal system.

Vesicle Compositions

The invention provides the vesicles that are spontaneously released into culture medium by bacteria of the invention. These vesicles are distinct from the vesicles that can be prepared artificially from the same bacteria, such as the sarkosyl-extracted OMVs prepared in reference 25 from 'ΔGNA33' meningococci. They are also distinct from microvesicles (MVs [47]) and 'native OMVs' ('NOMVs' [64]), although vesicles of the invention seem to be more similar to MVs and NOMVs than to sarkosyl-extracted OMVs. The vesicles are also distinct from blebs, which are outer-membrane protrusions that remain attached to bacteria prior to release as MVs [48,49].

The vesicles of the invention have a diameter of 50-100 nm by electron microscopy, which is smaller than that of artificial meningococcal OMVs (diameter ~270 nm [50]). The diameter is roughly the same as that of artificial OMVs that have been heat-denatured (~105 nm [50]), but the vesicles of the invention retain antigenicity whereas heat-denatured artificial OMVs lose their antigenicity. Moreover, vesicles of the invention (unlike MVs, OMVs and NOMVs) are substantially free from cytoplasmic contamination.

Vesicles of the invention preferably contain no more than 20% by weight of LOS/LPS, measured relative to the total protein (i.e. there should be at least 4× more protein than LOS/LPS, by weight). The maximum LOS/LPS level is preferably even lower than 20% e.g. 15%, 10%, 5% or lower.

Unlike the starting culture, the vesicle-containing compositions of the invention will generally be substantially free from whole bacteria, whether living or dead. The size of the vesicles of the invention means that they can readily be separated from whole bacteria by filtration through a 0.22 μm filter e.g. as typically used for filter sterilisation. Thus the invention provides a process for preparing vesicles of the invention, comprising filtering the culture medium from bacteria of the invention through a filter that retards whole bacteria but that lets the vesicles pass through e.g. a 0.22 μm filter. Although vesicles will pass through a standard 0.22 μm filters, these can rapidly become clogged by other material, and so it is preferred to perform sequential steps of filter sterilisation through a series of filters of decreasing pore size, finishing with a standard sterilisation filter (e.g. a 0.22 μm filter). Examples of preceding filters would be those with pore size of 0.8 μm, 0.45 μm, etc. The filtrate can be further treated e.g. by ultracentrifugation.

Vesicles of the invention contain lipids and proteins. The protein content of meningococcal vesicles has been analysed, and substantially all of the proteins in the vesicles are classified as outer membrane proteins by bioinformatic analysis. Outer membrane proteins seen in the vesicles include: PilE; IgA-specific serine endopeptidase; PorA; FrpB; P1B; etc. Unlike artificial OMVs, which have previously been analysed proteomically [51], the vesicles of the invention were found to lack proteins such as MinD, FtsA and phosphoenolpyruvate synthase. The vesicles also lack MltA.

The vesicles of the invention are advantageous when compared to vesicles prepared by disruption of cultured bacteria because no artificial disruption is required. Simple size-based separation can be used to separate bacteria and vesicles, without any need for chemical treatments, etc. As well as being a simpler process, this avoids the risk of denaturation caused by the detergents etc. that are used during prior art OMV preparative processes.

As mentioned above, vesicles of the invention may be similar to microvesicles (MVs) and 'native OMVs' ('NOMVs'), which are naturally-occurring membrane vesicles that form spontaneously during bacterial growth and are released into culture medium. MVs can be obtained by culturing *Neisseria* in broth culture medium, separating whole cells from the broth culture medium (e.g. by filtration or by low-speed centrifugation to pellet only the cells and not the smaller vesicles) and then collecting the MVs that are present in the cell-depleted medium (e.g. by filtration, by differential precipitation or aggregation of MVs, by high-speed centrifugation to pellet the MVs). Strains for use in production of MVs can generally be selected on the basis of the amount of MVs produced in culture. References 52 and 53 describe *Neisseria* with high MV production.

Vesicle Combinations

The invention allows the production of immunogenic vesicles from a bacterium of choice. The bacterium will typically have been generated by mutation of a chosen starting strain. Where there are multiple starting strains of interest then the invention provides methods for preparing vesicles from each of the strains, and the different vesicles can be combined. This combination strategy is particularly useful for bacteria where strain-to-strain variation means that a single strain usually does not offer clinically-useful protection e.g. serogroup B meningococcus.

Thus the invention provides a composition comprising a mixture of n sets of vesicles of the invention, prepared from n different strains of a bacterium. The value of n can be 1, 2, 3, 4, 5, etc. The different strains can be in the same or different serogroups. Preferred mixtures of serogroups include: A+B; A+C; A+W135; A+Y; B+C; B+W135; B+Y; C+W135; C+Y; W135+Y; A+B+C; A+B+W135; A+B+Y; A+C+W135; A+C+Y; A+W135+Y; B+C+W135; B+C+Y; C+W135+Y; A+B+C+W135; A+B+C+Y; B+C+W135+Y; and A+B+C+W135+Y.

The invention also provides a kit comprising vehicles of the invention prepared from n different strains of a bacterium. The vesicles can be kept and stored separately in the kit until they are required to be used together e.g. as an admixture, or for simultaneous separate or sequential use.

The invention also provides a process comprising: preparing n sets of vesicles of the invention, one from each of n different strains of a bacterium; and combining the n sets of vesicles. The different sets can be combined into a kit or into an admixture.

The invention also provides the use of vesicles from a first strain of a bacterium in the manufacture of a medicament for immunising a patient, wherein the medicament is administered simultaneously separately or sequentially with vesicles from a second strain of the bacterium.

The invention also the use of vesicles from a first strain of a bacterium in the manufacture of a medicament for immunising a patient, wherein the patient has been pre-immunised with vesicles from a second strain of the bacterium.

The bacterium is preferably *N.meningitidis*, and is more preferably from serogroup B. The different strains may be selected according to various criteria. Example criteria include: subtype and/or serosubtype [e.g. ref. 47]; immunotype; geographical origin of the strains; local prevalence of clinical strains; hypervirulent lineage e.g. one or more of subgroups I, III and IV-1, ET-5 complex, ET-37 complex, A4 cluster and lineage 3; multilocus sequence type (MLST) [54].

Preferred criteria for selecting strains are: selection of more than one PorB serotype (class 2 or 3 OMP); selection of more than one PorA serosubtype (class 1 OMP); selection of more than one different immunotype (lipopolysaccharide or lipooligosaccharide); selection of more than one of the three different NMB1870 variants [55]. NMB1870 is seen in the vesicles of the invention, shows distinct variants, and is a good candidate antigen for vaccination [55-57]. A combination of vesicles covering two or three different NMB1870 variants is particular advantageous.

As well as being selected from different meningococcal strains, vesicles can be selected from different pathogens. Thus the invention provides a composition comprising a mixture of n sets of vesicles of the invention, prepared from n different species of bacteria. Similarly, the invention provides a kit comprising vesicles of the invention prepared from n different species of bacteria, and provides a process comprising the step of preparing n sets of vesicles of the invention, one from each of n different species of bacteria.

MltA Expression

Bacteria of the invention do not possess functional MltA enzymatic activity. Prevention of MltA protein expression can be achieved in two main ways: removal or disruption of the endogenous mltA gene (including its control regions) to give a MltA⁻ strain; or suppression of MltA expression in a MltA⁺ strain. It is preferred to use a MltA⁻ strain.

MltA⁻ strains can be constructed by conventional knockout techniques. Techniques for gene knockout are well known, and meningococcus knockout mutants of have been reported previously [e.g. refs. 25 & 58-60]. The knockout is preferably achieved by deletion of at least a portion of the coding region (preferably isogenic deletion), but any other suitable technique may be used e.g. deletion or mutation of the promoter, deletion or mutation of the start codon, etc. The bacterium may contain a marker gene in place of the knocked out gene e.g. an antibiotic resistance marker.

Where suppression of expression from an endogenous mltA gene is used then techniques such as antisense inhibition and inhibitory RNA can be used, although these techniques are more typically used in eukaryotic hosts. In the resulting bacterium, mRNA encoding the knocked-out protein will be substantially absent and/or its translation will be substantially inhibited (e.g. to less than 1% of the level of expression that would be seen in the absence of suppression).

As an alternative to knockout or suppression of expression, site-directed mutagenesis of the endogenous mltA gene can be used. Reference 61 discloses mutants of meningococcal MltA in which residues Glu255, Glu323 and Asp362 were mutated and then tested for MltA catalytic activity. An E255G mutant of showed a 50% reduction in activity, and an E323G mutant showed a 70% reduction in activity. Mutagenesis of specific residues within the MltA coding region can therefore be used as a technique to knockout the lytic transglycolase enzymatic activity without knocking out the coding region.

Whichever technique (or combination of techniques) is chosen, the resulting bacterium will be substantially free from MltA enzymatic activity.

Pharmaceutical Compositions

The invention provides a pharmaceutical composition comprising (a) vesicles of the invention and (b) a pharmaceutically acceptable carrier. The invention also provides a process for preparing such a composition, comprising the step of admixing vesicles of the invention with a pharmaceutically acceptable carrier.

Typical 'pharmaceutically acceptable carriers' include any carrier that does not itself induce the production of antibodies harmful to the individual receiving the composition. Suitable carriers are typically large, slowly metabolised macromolecules such as proteins, polysaccharides, polylactic acids, polyglycolic acids, polymeric amino acids, amino acid copolymers, and lipid aggregates (such as oil droplets or liposomes). Such carriers are well known to those of ordinary skill in the art. The vaccines may also contain diluents, such as water, saline, glycerol, etc. Additionally, auxiliary substances, such as wetting or emulsifying agents, pH buffering substances, sucrose, and the like, may be present. Sterile pyrogen-free, phosphate-buffered physiologic saline (e.g. pH 7.4) is a typical carrier. A thorough discussion of pharmaceutically acceptable excipients is available in reference 62.

Compositions of the invention will typically be in aqueous form (i.e. solutions or suspensions) rather than in a dried form (e.g. lyophilised). Aqueous compositions are also suitable for reconstituting other vaccines from a lyophilised form (e.g. a lyophilised Hib conjugate vaccine, a lyophilised meningococcal conjugate vaccine, etc.). Where a composition of the invention is to be used for such extemporaneous reconstitution, the invention provides a kit, which may comprise two vials, or may comprise one ready-filled syringe and one vial, with the aqueous contents of the syringe being used to reactivate the dried contents of the vial prior to injection.

Compositions of the invention may be presented in vials, or they may be presented in ready-filled syringes. The syringes may be supplied with or without needles. Compositions may be packaged in unit dose form or in multiple dose form. A syringe will generally include a single dose of the composition, whereas a vial may include a single dose or multiple doses. For multiple dose forms, therefore, vials are preferred to pre-filled syringes.

Effective dosage volumes can be routinely established, but a typical human dose of the composition has a volume of about 0.5 ml e.g. for intramuscular injection. The RIVM OMV-based vaccine was administered in a 0.5 ml volume [63] by intramuscular injection to the thigh or upper arm. Similar doses may be used for other delivery routes e.g. an intranasal OMV-based vaccine for atomisation may have a volume of about 100 µl or about 130 µl per spray [64], with four sprays administered to give a total dose of about 0.5 ml.

The pH of the composition is preferably between 6 and 8, and more preferably between 6.5 and 7.5 (e.g. about 7 or about 7.4). The pH of the RIVM OMV-based vaccine is 7.4 [65], and a pH <8 (preferably <7.5) is preferred for compositions of the invention. Stable pH may be maintained by the use of a buffer e.g. a Tris buffer, a phosphate buffer, or a histidine buffer. Compositions of the invention will generally include a buffer. If a composition comprises an aluminium hydroxide salt, it is preferred to use a histidine buffer [66] e.g. at between 1-10 mM, preferably about 5 mM. The RIVM OMV-based vaccine maintains pH by using a 10 mM Tris/HCl buffer. The composition may be sterile and/or pyrogen-free. Compositions of the invention may be isotonic with respect to humans.

Compositions of the invention are immunogenic, and are more preferably vaccine compositions. Vaccines according to the invention may either be prophylactic (i.e. to prevent infection) or therapeutic (i.e. to treat infection), but will typically be prophylactic. Immunogenic compositions used as vaccines comprise an immunologically effective amount of antigen(s), as well as any other components, as needed. By 'immunologically effective amount', it is meant that the administration of that amount to an individual, either in a single dose or as part of a series, is effective for treatment or prevention. This amount varies depending upon the health and physical condition of the individual to be treated, age, the taxonomic group of individual to be treated (e.g. non-human primate, primate, etc.). the capacity of the individual's immune system to synthesise antibodies, the degree of protection desired, the formulation of the vaccine, the treating doctor's assessment of the medical situation, and other relevant factors. It is expected that the amount will fall in a relatively broad range that can be determined through routine trials. The antigen content of compositions of the invention will generally be expressed in terms of the amount of protein per dose. A dose of about 0.9 mg protein per ml is typical for OMV-based intranasal vaccines [64]. The MeNZB™ OMV-based vaccine contains between 25 and 200 µg of protein per millilitre e.g. between 45 and 90 µg/ml, or 50±10 µg/ml. Compositions of the invention preferably include less than 100 µg/ml of OMV per strain of bacterium.

Meningococci affect various areas of the body and so the compositions of the invention may be prepared in various forms. For example, the compositions may be prepared as injectables, either as liquid solutions or suspensions. The composition may be prepared for pulmonary administration e.g. as an inhaler, using a fine powder or a spray. The composition may be prepared as a suppository or pessary. The composition may be prepared for nasal, aural or ocular administration e.g. as spray, drops, gel or powder [e.g. refs. 67 & 68].

Compositions of the invention may include an antimicrobial, particularly when packaged in multiple dose format. Antimicrobials such as thiomersal and 2-phenoxyethanol are commonly found in vaccines, but it is preferred to use either a mercury-free preservative or no preservative at all.

Compositions of the invention may comprise detergent e.g. a Tween (polysorbate), such as Tween 80. Detergents are generally present at low levels e.g. <0.01%.

Compositions of the invention may include sodium salts (e.g. sodium chloride) to give tonicity. A concentration of 10±2 mg/ml NaCl is typical. The concentration of sodium chloride is preferably greater than 7.5 mg/ml.

Compositions of the invention will generally be administered in conjunction with other immunoregulatory agents. In particular, compositions will usually include one or more adjuvants, and the invention provides a process for preparing a composition of the invention, comprising the step of admixing vesicles of the invention with an adjuvant e.g. in a pharmaceutically acceptable carrier. Suitable adjuvants include, but are not limited to:

A. Mineral-Containing Compositions

Mineral containing compositions suitable for use as adjuvants in the invention include mineral salts, such as aluminium salts and calcium salts. The invention includes mineral salts such as hydroxides (e.g. oxyhydroxides), phosphates (e.g. hydroxyphosphates, orthophosphates), sulphates, etc. [e.g. see chapters 8 & 9 of ref. 69], or mixtures of different mineral compounds, with the compounds taking any suitable form (e.g. gel, crystalline, amorphous, etc.), and with adsorption being preferred. The mineral containing compositions may also be formulated as a particle of metal salt [70].

A typical aluminium phosphate adjuvant is amorphous aluminium hydroxyphosphate with $PO_4$/Al molar ratio between 0.84 and 0.92, included at 0.6 mg $Al^{3+}$/ml. Adsorption with a low dose of aluminium phosphate may be used e.g. between 50 and 100 µg $Al^{3+}$ per conjugate per dose. Where an aluminium phosphate it used and it is desired not to adsorb an antigen to the adjuvant, this is favoured by including free phosphate ions in solution (e.g. by the use of a phosphate buffer).

The RIVM vaccine was tested with adsorption to either an aluminium phosphate or an aluminium hydroxide adjuvant, and the aluminium phosphate adjuvant was found to give superior results [65]. The MeNZB™, MenBvac™ abd VA-MENINGOC-BC™ products all include an aluminium hydroxide adjuvant.

A typical dose of aluminium adjuvant is about 3.3 mg/ml (expressed as $Al^{3+}$ concentration).

B. Oil Emulsions

Oil emulsion compositions suitable for use as adjuvants in the invention include squalene-water emulsions, such as MP59 [Chapter 10 of ref. 69; see also ref. 71] (5% Squalene, 0.5% Tween 80, and 0.5% Span 85, formulated into submicron particles using a microfluidizer). Complete Freund's adjuvant (CFA) and incomplete Freund's adjuvant (IFA) may also be used.

C. Saponin Formulations [Chapter 22 of Ref. 69]

Saponin formulations may also be used as adjuvants in the invention. Saponins are a heterologous group of sterol glycosides and triterpenoid glycosides that are found in the bark, leaves, stems, roots and even flowers of a wide range of plant species. Saponin from the bark of the *Quillaia saponaria* Molina tree have been widely studied as adjuvants. Saponin can also be commercially obtained from *Smilax ornata* (sarsaprilla), *Gypsophilla panicitlata* (brides veil), and *Saponaria officianalis* (soap root). Saponin adjuvant formulations include purified formulations, such as QS21, as well as lipid formulations, such as ISCOMs. QS21 is marketed as Stimulon™.

Saponin compositions have been purified using HPLC and RP-HPLC. Specific purified factions using these techniques have been identified, including QS7, QS17, QS18, QS21, QH-A, QH-B and QH-C. Preferably, the saponin is QS21. A method of production of QS21 is disclosed in ref. 72. Saponin formulations may also comprise a sterol, such as cholesterol [73].

Combinations of saponins and cholesterols can be used to form unique particles called immunostimulating complexes (ISCOMs) [chapter 23 of ref. 69]. ISCOMs typically also include a phospholipid such as phosphatidylethanolamine or phosphatidylcholine. Any known saponin can be used in ISCOMs. Preferably, the ISCOM includes one or more of QuilA, QHA and QHC. ISCOMs are further described in refs. 73-75. Optionally, the ISCOMS may be devoid of extra detergent [76].

A review of the development of saponin based adjuvants can be found in refs. 77 & 78.

D. Virosomes and Virus-Like Particles

Virosomes and virus-like particles (VLPs) can also be used as adjuvants in the invention. These structures generally contain one or more proteins from a virus optionally combined or formulated with a phospholipid. They are generally non-pathogenic, non-replicating and generally do not contain any of the native viral genome. The viral proteins may be recombinantly produced or isolated from whole viruses. These viral proteins suitable for use in virosomes or VLPs include proteins derived from influenza virus (such as HA or NA), Hepatitis B virus (such as core or capsid proteins), Hepatitis E virus, measles virus, Sindbis virus, Rotavirus, Foot-and-Mouth Disease virus, Retrovirus, Norwalk virus, human Papilloma virus, HIV, RNA-phages, Qβ-phage (such as coat proteins), GA-phage, fr-phage, AP205 phage, and Ty (such as retrotransposon Ty protein p1). VLPs are discussed further in refs. 79-84. Virosomes are discussed further in, for example, ref. 85

E. Bacterial or Microbial Derivatives

Adjuvants suitable for use in the invention include bacterial or microbial derivatives such as non-toxic derivatives of enterobacterial lipopolysaccharide (LPS), Lipid A derivatives, immunostimulatory oligonucleotides and ADP-ribosylating toxins and detoxified derivatives thereof.

Non-toxic derivatives of LPS include monophosphoryl lipid A (MPL) and 3-O-deacylated MPL (3dMPL). 3dMPL is a mixture of 3 de-O-acylated monophosphoryl lipid A with 4, 5 or 6 acylated chains. A preferred "small particle" form of 3 De-O-acylated monophosphoryl lipid A is disclosed in ref. 86. Such "small particles" of 3dMPL are small enough to be sterile filtered through a 0.22 μm membrane [86]. Other non-toxic LPS derivatives include monophosphoryl lipid A mimics, such as aminoalkyl glucosaminide phosphate derivatives e.g. RC-529 [87,88].

Lipid A derivatives include derivatives of lipid A from *Escherichia coli* such as OM-174. OM-174 is described for example in refs. 89 & 90.

Immunostimulatory oligonucleotides suitable for use as adjuvants in the invention include nucleotide sequences containing a CpG motif (a dinucleotide sequence containing an unmethylated cytosine linked by a phosphate bond to a guanosine). Double-stranded RNAs and oligonucleotides containing palindromic or poly(dG) sequences have also been shown to be immunostimulatory.

The CpG's can include nucleotide modifications/analogs such as phosphorothioate modifications and can be double-stranded or single-stranded. References 91, 92 and 93 disclose possible analog substitutions e.g. replacement of guanosine with 2'-deoxy-7-deazaguanosine. The adjuvant effect of CpG oligonucleotides is further discussed in refs. 94-99.

The CpG sequence may be directed to TLR9, such as the motif GTCGTT or TTCGTT [100]. The CpG sequence may be specific for inducing a Th1 immune response, such as a CpG-A ODN, or it may be more specific for inducing a B cell response, such a CpG-B ODN. CpG-A and CpG-B ODNs are discussed in refs. 101-103. Preferably, the CpG is a CpG-A ODN.

Preferably, the CpG oligonucleotide is constructed so that the 5' end is accessible for receptor recognition. Optionally, two CpG oligonucleotide sequences may be attached at their 3' ends to form "immunomers". See, for example, refs. 100 & 104-106.

Bacterial ADP-ribosylating toxins and detoxified derivatives thereof may be used as adjuvants in the invention. Preferably, the protein is derived from *E.coli* (*E.coli* heat labile enterotoxin "LT"), cholera ("CT"), or pertussis ("PT"). The use of detoxified ADP-ribosylating toxins as mucosal adjuvants is described in ref. 107 and as parenteral adjuvants in ref. 108. The toxin or toxoid is preferably in the form of a holotoxin, comprising both A and B subunits. Preferably, the A subunit contains a detoxifying mutation; preferably the B subunit is not mutated. Preferably, the adjuvant in a detoxified LT mutant such as LT-K63, LT-R72, and LT-G192. The use of ADP-ribosylating toxins and detoxified derivaties thereof, particularly LT-K63 and LT-R72, as adjuvants can be found in refs. 109-116. Numerical reference for amino acid substitutions is preferably based on the alignments of the A and B subunits of ADP-ribosylating toxins set forth in ref. 117, specifically incorporated herein by reference in its entirety.

F. Human Immunomodulators

Human immunomodulators suitable for use as adjuvants in the invention include cytokines, such as interleukins (e.g. IL-1, IL-2, IL-4, IL-5, IL-6, IL-7, IL-12 [118], etc.) [119], interferons (e.g. interferon-γ), macrophage colony stimulating factor, and tumor necrosis factor.

G. Bioadhesives and Mucoadhesives

Bioadhesives and mucoadhesives may also be used as adjuvants in the invention. Suitable bioadhesives include esterified hyaluronic acid microspheres [120] or mucoadhesives such as cross-linked derivatives of poly(acrylic acid), polyvinyl alcohol, polyvinyl pyrollidone, polysaccharides and carboxymethylcellulose. Chitosan and derivatives thereof may also be used as adjuvants in the invention [121].

H. Microparticles

Microparticles may also be used as adjuvants in the invention. Microparticles (i.e. a particle of ~100 nm to ~150 μm in diameter, more preferably ~200 nm to ~30 μm in diameter, and most preferably ~500 nm to ~10 μm in diameter) formed from materials that are biodegradable and non-toxic (e.g. a poly(a-hydroxy acid), a polyhydroxybutyric acid, a polyorthoester, a polyanhydride, a polycaprolactone, etc.), with poly(lactide-co-glycolide) are preferred, optionally treated to have a negatively-charged surface (e.g. with SDS) or a positively-charged surface (e.g. with a cationic detergent, such as CTAB).

I. Liposomes (Chapters 13 & 14 of Ref. 69)

Examples of liposome formulations suitable for use as adjuvants are described in refs. 122-124.

J. Polyoxyethylene Ether and Polyoxyethylene Ester Formulations

Adjuvants suitable for use in the invention include polyoxyethylene ethers and polyoxyethylene esters [125]. Such formulations further include polyoxyethylene sorbitan ester surfactants in combination with an octoxynol [126] as well as polyoxyethylene alkyl ethers or ester surfactants in combination with at least one additional non-ionic surfactant such as an octoxynol [127]. Preferred polyoxyethylene ethers are selected from the following group: polyoxyethylene-9-lauryl ether (laureth 9), polyoxyethylene-9-steoryl ether, polyoxytheylene-8-steoryl ether, polyoxyethylene-4-lauryl ether, polyoxyethylene-35-lauryl ether, and polyoxyethylene-23-lauryl ether.

K. Polyphosphazene (PCPP)

PCPP formulations are described, for example, in refs. 128 and 129.

L. Muramyl Peptides

Examples of muramyl peptides suitable for use as adjuvants in the invention include N-acetyl-muramyl-L-threonyl-D-isoglutamine (thr-MDP), N-acetyl-normuramyl-L-alanyl-D-isoglutamine (nor-MDP), and N-acetylmuramyl-L-alanyl-D-isoglutaminyl-L-alanine-2-(1'-2'-dipalmitoyl-sn-glycero-3-hydroxyphosphoryloxy)-ethylamine MTP-PE).

M. Imidazoquinolone Compounds.

Examples of imidazoquinolone compounds suitable for use adjuvants in the invention include Imiquamod and its homologues (e.g. "Resiquimod 3M"), described further in refs. 130 and 131.

The invention may also comprise combinations of aspects of one or more of the adjuvants identified above. For example, the following adjuvant compositions may be used in the invention: (1) a saponin and an oil-in-water emulsion [132]; (2) a saponin (e.g. QS21)+a non-toxic LPS derivative (e.g. 3dMPL [133]; (3) a saponin (e.g. QS21)+a non-toxic LPS derivative (e.g. 3dMPL)+a cholesterol; (4) a saponin (e.g. QS21)+3dMPL+IL-12 (optionally+a sterol) [134]; (5) combinations of 3dMPL with, for example, QS21 and/or oil-in-water emulsions [135]; (6) SAF, containing 10% squalane, 0.4% Tween 80™, 5% pluronic-block polymer L12I, and thr-MDP, either microfluidized into a submicron emulsion or vortexed to generate a larger particle size emulsion. (7) Ribi™ adjuvant system (RAS), (Ribi Immunochem) containing 2% squalene, 0.2% Tween 80, and one or more bacterial cell wall components from the group consisting of monophosphorylipid A (MPL), trehalose dimycolate (TDM), and cell wall skeleton (CWS), preferably MPL+CWS (Detox™); and (8) one or more mineral salts (such as an aluminum salt)+a non-toxic derivative of LPS (such as 3dMPL).

Other substances that act as immunostimulating agents are disclosed in chapter 7 of ref. 69.

The use of aluminium salt adjuvants is particularly preferred, and antigens are generally adsorbed to such salts. It is possible in compositions of the invention to adsorb some antigens to an aluminium hydroxide but to have other antigens in association with an aluminium phosphate. In general, however, it is preferred to use only a single salt e.g. a hydroxide or a phosphate, but not both. Not all vesicles need to be adsorbed i.e. some or all can be free in solution.

Methods of Treatment

The invention also provides a method for raising an immune response in a mammal, comprising administering a pharmaceutical composition of the invention to the mammal. The immune response is preferably protective and preferably involves antibodies. The method may raise a booster responsein a patient that has already been primed against N.meningitidis. Subcutaneous and intranasal prime/boost regimes for OMVs are disclosed in ref. 136.

The mammal is preferably a human. Where the vaccine is for prophylactic use, the human is preferably a child (e.g. a toddler or infant) or a teenager; where the vaccine is for therapeutic use, the human is preferably an adult. A vaccine intended for children may also be administered to adults e.g. to assess safety, dosage, immunogenicity, etc.

The invention also provides vesicles of the invention for use as a medicament. The medicament is preferably able to raise an immune response in a mammal (i.e. it is an immunogenic composition) and is more preferably a vaccine.

The invention also provides the use of vesicles of the invention in the manufacture of a medicament for raising an immune response in a mammal.

The invention also the use of vesicles of the invention in the manufacture of a medicament for immunising a patient, wherein the patient has been pre-immunised with at least one of the following: diphtheria toxoid; tetanus toxoid; acellular or cellular pertussis antigens; a conjugated Hib capsular saccharide; hepatitis B virus surface antigen; a conjugated meningococcal capsular saccharide; and/or a conjugated pneumococcal capsular saccharide.

These uses and methods are preferably for the prevention and/or treatment of a disease caused by N.meningitidis e.g. bacterial (or, more specifically, meningococcal) meningitis, of septicemia.

One way of checking efficacy of therapeutic treatment involves monitoring Neisserial infection after administration of the composition of the invention. One way of checking efficacy of prophylactic treatment involves monitoring immune responses against the vesicles' antigens after administration of the composition. Immunogenicity of compositions of the invention can be determined by administering them to test subjects (e.g. children 12-16 months age, or animal models [137]) and then determining standard parameters including serum bactericidal antibodies (SBA) and ELISA titres (GMT). These immune responses will generally be determined around 4 weeks after administration of the composition, and compared to values determined before administration of the composition. A SBA increase of at least 4-fold or 8-fold is preferred. Where more than one dose of the composition is administered, more than one post-administration determination may be made.

Preferred compositions of the invention can confer an antibody titre in a patient that is superior to the criterion for seroprotection for an acceptable percentage of human subjects. Antigens with an associated antibody titre above which a host is considered to be seroconverted against the antigen are well known, and such titres are published by organisations such as WHO. Preferably more than 80% of a statistically significant sample of subjects is seroconverted, more preferably more than 90%, still more preferably more than 93% and most preferably 96-100%.

Compositions of the invention will generally be administered directly to a patient. Direct delivery may be accomplished by parenteral injection (e.g. subcutaneously, intraperitoneally, intravenously, intramuscularly, or to the interstitial space of a tissue), or by rectal, oral, vaginal, topical, transdermal, intranasal, ocular, aural, pulmonary or other mucosal administration. Intramuscular administration to the thigh or the upper arm is preferred. Injection may be via a needle (e.g. a hypodermic needle), but needle-free injection may alternatively be used. A typical intramuscular dose is 0.5 ml.

Dosage treatment can be a single dose schedule or a multiple dose schedule. Multiple doses may be used in a primary immunisation schedule and/or in a booster immunisation schedule. A primary dose schedule may be followed by a booster dose schedule. Suitable timing between priming doses (e.g. between 4-16 weeks), and between priming and boosting, can be routinely determined. The OMV-based RIVM vaccine was tested using a 3- or 4-dose primary schedule, with vaccination at 0, 2 & 8 or 0, 1, 2 & 8 months. MeNZB™ is administered as three doses at six week intervals. These schedules can be used according to the invention. The vesicle preparations given at each dose stage can be the same or different.

In methods of the invention, where a first dose is given at time zero then a second and a third dose may be given over the next two months, and a fourth dose may be given between 11 and 13 months after time zero. The first, second and third doses may comprise vesicles with the same serosubtype as each other, and the fourth dose may comprises vesicles with a different serosubtype from the first three doses. The fourth dose may contain vesicles only with a different serosubtype from the first three doses, or it may contain two types of vesicle, one with a different serosubtype from the first three doses and one with the same subtype. The first, second and third doses are preferably given at intervals of between 6 and 8 weeks. The fourth dose is preferably given about 1 year after time zero. The patient preferably receives the same quantity of vaccine at each of the four doses.

As described above, the invention may involve administration of vesicles from more than one subtype and/or serosubtype of N.meningitidis [e.g. ref. 47], either separately or in admixture.

The invention may be used to elicit systemic and/or mucosal immunity.

In general, compositions of the invention are able to induce serum bactericidal antibody responses after being administered to a subject. These responses are conveniently measured in mice and are a standard indicator of vaccine efficacy [e.g. see end-note 14 of reference 196]. Serum bactericidal activity (SBA) measures bacterial killing mediated by complement, and can be assayed using human or baby rabbit complement. WHO standards require a vaccine to induce at least a 4-fold rise in SBA in more than 90% of recipients. MeNZB™ elicits a 4-fold rise in SBA 4-6 weeks after administration of the third dose.

Rather than offering narrow protection, compositions of the invention can induce bactericidal antibody responses against more than one hypervirulent lineage of serogroup B. In particular, they can preferably induce bactericidal responses against two or three of the following three hypervirulent lineages: (i) cluster A4; (ii) ET5 complex; and (iii) lineage 3. They may additionally induce bactericidal antibody responses against one or more of hypervirulent lineages subgroup I, subgroup III, subgroup IV-1 or ET-37 complex, and against other lineages e.g. hyperinvasive lineages. This does not necessarily mean that the composition can induce bactericidal antibodies against each and every strain of serogroup B meningococcus within these hypervirulent lineages e.g. rather, for any given group of four of more strains of serogroup B meningococcus within a particular hypervirulent linage, the antibodies induced by the composition are bactericidal against at least 50% (e.g. 60%, 70%, 80%, 90% or more) of the group. Preferred groups of strains will include strains isolated in at least four of the following countries: GB, AU, CA, NO, IT, US, NZ, NL, BR, and CU. The serum preferably has a bactericidal titre of at least 1024 (e.g. $2^{10}$, $2^{11}$, $2^{12}$, $2^{13}$, $2^{14}$, $2^{15}$, $2^{16}$, $2^{17}$, $2^{18}$ or higher, preferably at least $2^{34}$) e.g. the serum is able to kill at least 50% of test bacteria of a particular strain when diluted 1/1024, as described in reference 196.

Preferred compositions can induce bactericidal responses against the following strains of serogroup B meningococcus: (i) from cluster A4, strain 961-5945 (B:2b:P1.21,16) and/or strain G2136 (B:-); (ii) from ET-5 complex, strain MC58 (B:15:P1.7,16b) and/or strain 44/76 (B:15:P1.7,16); (iii) from lineage 3, strain 394/98 (B:4:P1.4) and/or strain BZ198 (B:NT:-). More preferred compositions can induce bactericidal responses against strains 961-5945, 44/76 and 394/98.

Strains 961-5945 and G2136 are both Neisseria MLST reference strains [ids 638 & 1002 in ref. 138]. Strain MC58 is widely available (e.g. ATCC BAA-335) and was the strain sequenced in reference 32. Strain 44/76 has been widely used and characterised (e.g. ref. 139) and is one of the Neisseria MLST reference strains [id 237 in ref. 138; row 32 of Table 2 in ref. 33]. Strain 394/98 was originally isolated in New Zealand in 1998, and there have been several published studies using this strain, (e.g. refs. 140 & 141). Strain BZ198 is another MLST reference strain [id 409 in ref. 138; row 41 of Table 2 in ref. 33].

Further Antigenic Components

As well as containing antigenic vesicles of the invention, compositions of the invention may include further non-vesicular antigens. For example, the composition may comprise one or more of the following further antigens saccharide antigen from N.meningitidis serogroup A, C, W135 and/or Y, such as the oligosaccharide disclosed in ref. 142 from serogroup C or the oligosaccharides of ref. 143. The VA-MENINGOC-BC™ product contains serogroup C polysaccharide.

a saccharide antigen from Streptococcus pneumoniae [e.g. refs. 144-146; chapters 22 & 23 of ref. 153].

an antigen from hepatitis A virus, such as inactivated virus [e.g. 147, 148; chapter 15 of ref. 153].

an antigen from hepatitis B virus, such as the surface and/or core antigens [e.g. 148,149; chapter 16 of ref. 153].

an antigen from hepatitis C virus [e.g. 150].

an antigen from Bordetella pertussis, such as pertussis holotoxin (PT) and filamentous haemagglutinin (FHA) from B.pertussis, optionally also in combination with pertactin and/or agglutinogens 2 and 3 [e.g. refs. 151 & 152; chapter 22 of ref. 153].

a diphtheria antigen, such as a diphtheria toxoid [e.g. chapter 13 of ref. 153].

a tetanus antigen, such as a tetanus toxoid [e.g. chapter 27 of ref. 153].

a saccharide antigen from Haemophilus influenzae B [e.g. chapter 14 of ref. 153]

an antigen from N.gonorrhoeae [e.g. ref. 154].

an antigen from Chlamydia pneumoniae [e.g. 155-161].

an antigen from Chlamydia trachomatis [e.g. 162].

an antigen from Porphyromonas gingivalis [e.g. 163].

polio antigen(s) [e.g. 164, 165; chapter 24 of ref. 153] such as IPV.

rabies antigen(s) [e.g. 166] such as lyophilised inactivated virus [e.g. 167, RabAvert™].

measles, mumps and/or rubella antigens [e.g. chapters 19, 20 and 26 of ref. 153].

influenza antigen(s) [e.g. chapters 17 & 18 of ref. 153], such as the haemagglutinin and/or neuraminidase surface proteins.

an antigen from Moraxella catarrhalis [e.g. 168].

a protein antigen from Streptococcus agalactiae (group B streptococcus) [e.g. 169, 170].

an antigen from Streptococcus pyogenes (group A streptococcus) [e.g. 170, 171, 172].

Where a saccharide or carbohydrate antigen is used, it is preferably conjugated to a carrier in order to enhance immunogenicity. Conjugation of *H.influenzae* B, meningococcal and pneumococcal saccharide antigens is well known.

Toxic protein antigens may be detoxified where necessary (e.g. detoxification of pertussis toxin by chemical and/or generic means [152]).

Where a diphtheria antigen is included in the composition it is preferred also to include tetanus antigen and pertussis antigens. Similarly, where a tetanus antigen is included it is preferred also to include diphtheria and pertussis antigens. Similarly, where a pertussis antigen is included it is preferred also to include diphtheria and tetanus antigens. DTP combinations are thus preferred.

Saccharide antigens are preferably in the form of conjugates. Preferred carrier proteins for conjugates are bacterial toxins or toxoids, such as diphtheria toxoid or tetanus toxoid. The CRM197 mutant of diphtheria toxin [173-175] is a particularly preferred carrier for, as is a diphtheria toxoid. Other suitable carrier proteins include the *N.meningitidis* outer membrane protein [176], synthetic peptides [177,178], heat shock proteins [179,180], pertussis proteins [181,182], cytokines [183], lymphokines [183], hormones [183], growth factors [183], artificial proteins comprising multiple human CD4+ T cell epitopes from various pathogen-derived antigens [184] such as N19, protein D from *H.influenzae* [185,186], pneumococcal surface protein PspA [187], pneumolysin [188], iron-uptake proteins [189], toxin A or B from *C.difficile* [190], etc.

Preferred compositions include meningococcal Vesicles as described above, plus a conjugated capsular saccharide from one or more (i.e. 1, 2, 3 or 4) of meningococcal serogroups A, C, W135 and Y. Where the Vesicles are from serogroup B then this approach allows the following serogroups to be covered: B+A; B+C; B+W135; B+Y; B+C+W135; B+C+Y; B+W135+Y; B+A+C+W135; B+A+C+Y; B+A+W135+Y; B+C+W135+Y; and B+A+C+W135+Y. Two preferred combinations use serogroup B Vesicles plus conjugate antigens from either serogroups A+W135+Y or serogroups A+C+W135+Y. In general, it is possible to cover all five of serogroups A, B, C, W135 and Y by choosing Vesicles for x serogroup(s) and conjugated saccharides for the remaining 5-x serogroups.

Specific meningococcal protein antigens (preferably from serogroup B) may also be added to supplement the vesicle compositions. In particular, a protein antigen such as disclosed in refs. 41 & 191 to 199 may be added. A small number of defined antigens may be added (a mixture of 10 or fewer (e.g. 9, 8, 7, 6, 5, 4, 3, 2) purified antigens). Preferred additional immunogenic polypeptides for use with the invention are those disclosed in reference 199: (1) a 'NadA' protein; (2) a '741' protein; (3) a '936' protein; (4) a '953' protein; and (5) a '287' protein. Other possible supplementing meningococcal antigens include transferrin binding proteins (e.g. TbpA and TbpB) and/or Cu,Zn-superoxide dismutase [18]. Other possible supplementing meningococcal antigens include ORF40 (also known as 'Hsf' or 'NhhA' [200,201]), LetP [202] and ExbB [202]. Other possible supplementing meningococcal antigens include proteins comprising one of the following amino acid sequences: SEQ ID NO:650 from ref. 191; SEQ ID NO:878 from ref. 191; SEQ ID NO:884 from ref. 191; SEQ ID NO:4 from ref. 192; SEQ ID NO:598 from ref. 193; SEQ ID NO:818 from ref. 193; SEQ ID NO:864 from ref. 193; SEQ ID NO:866 from ref. 193; SEQ ID NO:1196 from ref. 193; SEQ ID NO:1272 from ref. 193; SEQ ID NO:1274 from ref. 193; SEQ ID NO:1640 from ref. 193; SEQ ID NO:1788 from ref. 193; SEQ ID NO:2288 from ref. 193; SEQ ID NO:2466 from ref. 193; SEQ ID NO:2554 from ref. 193; SEQ ID NO:2576 from ref. 193; SEQ ID NO:2606 from ref. 193; SEQ ID NO:2608 from ref. 193; SEQ ID NO:2616 from ref. 193; SEQ ID NO:2668 from ref. 193; SEQ ID NO:2780 from ref. 193; SEQ ID NO:2932 from ref. 193; SEQ ID NO:2958 from ref. 193; SEQ ID NO:2970 from ref. 193; SEQ ID NO:2988 from ref. 193, or a polypeptide comprising an amino acid sequence which: (a) has 50% or more identity (e.g. 60%, 70%, 80%, 90%, 95%, 99% or more) to said sequences; and/or (b) comprises a fragment of at least n consecutive amino acids from said sequences, wherein n is 7 or more (eg. 8, 10, 12, 14, 16, 18, 20, 25, 30, 35, 40, 50, 60, 70, 80, 90, 100, 150, 200, 250 or more). Preferred fragments for (b) comprise an epitope from the relevant sequence. More than one (e.g. 2, 3, 4, 5, 6) of these polypeptides may be included. The meningococcal antigens transferrin binding protein and/or Hsf protein may also be added [203].

Supplementation of the OMVs by defined meningococcal antigens in this way is particularly useful where the OMVs are from a serosubtype P1.7b,4 meningococcus or a serosubtype P1.7,16 meningococcus. Supplementation of a mixture of OMVs from both these serosubtypes is preferred.

It is also possible to add vesicles that are not vesicles of the invention e.g. OMVs, MVs, NOMVs, etc. that are prepared by methods other than those of the invention (e.g. prepared by methods involving disruption of bacterial membranes, as disclosed in the prior art).

Antigens in the composition will typically be present at a concentration of at least 1 μg/ml each. In general, the concentration of any given antigen will be sufficient to elicit an immune response against that antigen.

As an alternative to using protein antigens in the composition of the invention, nucleic acid encoding the antigen may be used. Protein components of the compositions of the invention may thus be replaced by nucleic acid (preferably DNA e.g. in the form of a plasmid) that encodes the protein.

New Meningococcal Proteins

The genome sequence of serogroup B meningococcus is reported in reference 32. The initial annotation of the genome has not been accepted for all of the >2000 genes e.g. the start codon on NMB1870 has subsequently been re-assigned [41,55]. The inventors have found that the start codons for NMB0928, NMB0109 and NMB1057 should also be re-assigned:

The original sequence of NMB0928 is shown in FIG. 6 (SEQ ID NO: 3). The inventors believe that the true start codon for NMB0928 in the ATG encoding the methionine at residue 24 of FIG. 6. With the new start codon (SEQ ID NO: 6), NMB0928 presents a typical signature of a surface-exposed protein, characterised by a signal peptide with a lipo-box motif (underlined).

The original sequence of NMB0109 is shown in FIG. 7 (SEQ ID NO: 4). The inventors believe that the true start codon for NMB0109 is the ATG encoding the Met at residue 39 of FIG. 7. (SEQ ID NO: 7)

The original sequence of NMB1057 is shown in FIG. 8 (SEQ ID NO: 5). The inventors believe that the true start codon for NMB1057 is the GTG encoding the Val at residue 14 of FIG. 8. (SEQ ID NO: 8)

Thus the invention provides a polypeptide comprising: (a) the amino acid sequence of SEQ ID NO:6; (b) an amino acid sequence having at least 50% (e.g. 60%, 70%, 80% 85%, 90%, 95%, 96%, 97%, 98%, 99%, 99.5% or more) sequence identity to SEQ ID NO:6, and/or comprising an amino acid sequence consisting of a fragment of at least 7 (e.g. 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 120, 140, 160, 180, 200, 225, 250) contiguous amino acids from SEQ ID NO:6. Preferred polypeptides have a N-terminus cysteine residue, preferably corresponding to Cys-19 of SEQ ID NO:6, and the N-terminus cysteine is preferably lipidated. Preferred polypeptides do not include the amino acid sequence MTHIKPVIAALALIGLAA (SEQ ID NO: 9) within 30 amino acids of their N-terminus.

The invention also provides a polypeptide comprising: (a) the amino acid sequence of SEQ ID NO:7; (b) an amino acid sequence having at least 50% (e.g. 60%, 70%, 80%, 85%, 90%, 95%, 96%, 97%, 98%, 99%, 99.5% or more) sequence identity to SEQ ID NO:7, and/or comprising an amino acid sequence consisting of a fragment of at least 7 (e.g. 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 120, 140, 160, 180, 200, 225, 250) contiguous amino acids from SEQ ID NO:7. Preferred polypeptides do not include the amino acid sequence MLKCGTFFITRHIPRGCRRFFQPNQAR-QTEIYQIRGTV (SEQ ID NO: 10) within 20 amino acids of their N-terminus.

The invention also provides a polypeptide comprising: (a) the amino acid sequence of SEQ ID NO:8; (b) an amino acid sequence having at least 50% (e.g. 60%, 70%, 80%, 85%, 90%, 95%, 96%, 97%, 98%, 99%, 99.5% or more) sequence identity to SEQ ID NO:8, and/or comprising an amino acid sequence consisting of a fragment of at least 7 (e.g. 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 120, 140, 160, 180, 200, 225, 250) contiguous amino acids from SEQ ID NO:8. Preferred polypeptides have a N-terminus cysteine residue, preferably corresponding to Cys-Gln of SEQ ID NO:8, and the N-terminus cysteine is preferably lipidated. Other preferred polypeptides do not include the amino acid sequence MPCMNHQSNS (SEQ ID NO: 11) within 20 amino acids of their N-terminus.

Polypeptides can be prepared by various means e.g. by chemical synthesis (at least in part), by digesting longer polypeptides using proteases, by translation from RNA, by purification from cell culture (e.g. from recombinant expression or from *N.meningitidis* culture), etc. Heterologous expression in an *E.coli* host is a preferred expression route.

Polypeptides of the invention may be attached or immobilised to a solid support. Polypeptides of the invention may comprise a detectable label e.g. a radioactive label, a fluorescent label, or a biotin label. This is particularly useful in immunoassay techniques.

Polypeptides can take various forma (e.g. native, fusions, glycosylated, non-glycosylated, lipidated, disulfide bridges, etc.). Polypeptides are preferably meningococcal polypeptides.

Polypeptides are preferably prepared in substantially pure or substantially isolated form (i.e. substantially free from other Neisserial or host cell polypeptides) or substantially isolated form. In general, the polypeptides are provided in a non-naturally occurring environment e.g. they are separated from their naturally-occurring environment. In certain embodiments, the subject polypeptide is present in a composition that is enriched for the polypeptide as compared to a control. As such, purified polypeptide is provided, whereby purified is meant that the polypeptide is present in a composition that is substantially free of other expressed polypeptides, where by substantially free is meant that less than 50%, usually less than 30% and more usually less than 10% of the composition is made up of other expressed polypeptides.

The term "polypeptide" refers to amino acid polymers of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. Polypeptides can occur as single chains or associated chains.

General

The term "comprising" encompasses "including" as well as "consisting" e.g. a composition "comprising" X may consist exclusively of X or may include something additional e.g. X+Y.

The term "about" in relation to a numerical value x means, for example, x±10%.

The word "substantially" does not exclude "completely" e.g. a composition which is "substantially free" from Y may be completely free from Y. Where necessary, the word "substantially" may be omitted from the definition of the invention.

References to a percentage sequence identity between two amino acid sequences means that, when aligned, that percentage of amino acids are the same in comparing the two sequences. This alignment and the percent homology or sequence identity can be determined using software programs known in the art, for example those described in section 7.7.18 of reference 204. A preferred alignment is determined by the Smith-Waterman homology search algorithm using an affine gap search with a gap open penalty of 12 and a gap extension penalty of 2, BLOSUM matrix of 62. The Smith-Waterman homology search algorithm is well known and is disclosed in reference 205.

References to 'NMB' proteins with a four digit number refers toB the standard nomenclature of reference 32, assigned on the basis of a genome sequence of a prototypic strain of serogroup B meningococcus. The public sequence databases include these NMB sequences- For any given meningococcus, the skilled person can readily and unambiguously find the gene corresponding to a NMBnnnn sequence by using the existing sequence from the database and/or the genetic environment of the NMBnnnn ORF in the prototype strain e.g. to design primers, probes, etc.

The terms 'GNA33', 'NMB0033' and 'mltA' can be used interchangeably when referring to meningococcus.

BRIEF DESCRIPTION OF DRAWINGS

FIG. 2B shows absorbance at 280 nm.

FIG. 3A is lower resolution electron microscopy (the bar shows 100 nm). FIG. 3B is higher resolution electron microscopy (the bar shows 50 nm).

FIGS. 4A-F shows western blot analysis of vesicles of the invention with six different antibodies. FIG. 4A shows mouse serum raised against OMVs prepared from the NZ strain by deoxycholate extraction. FIG. 4B shows mouse serum raised against ΔGNA33 knockout mutants. FIG. 4C shows mouse anti-PorA$_{P1.4}$ monoclonal. FIG. 4D shows mouse anti-NMB2132 serum. FIG. 4E shows mouse anti-NMB1030 serum. FIG. 4F shows mouse anti-NMB1870 serum.

In FIG. 7B the horizontal axis runs from pI 3 to 10 and the vertical axis runs from 10 to 200 kDa.

FIG. 8A shows two preparations of *E. coli* CFI073. FIG. 8B shows the *E. coli* strain preparations: DH5a, 536, and IHE3034.

FIGS. 9A and 9B are strain MC58. FIGS. 9C and 9D are strain NZ98/254.

FIGS. 10A-B show 1D SDS-PAGE and 2D SDS-PAGE (FIG. 10B) of vesicles from ΔmltA knockout meningococci.

Figure 1:
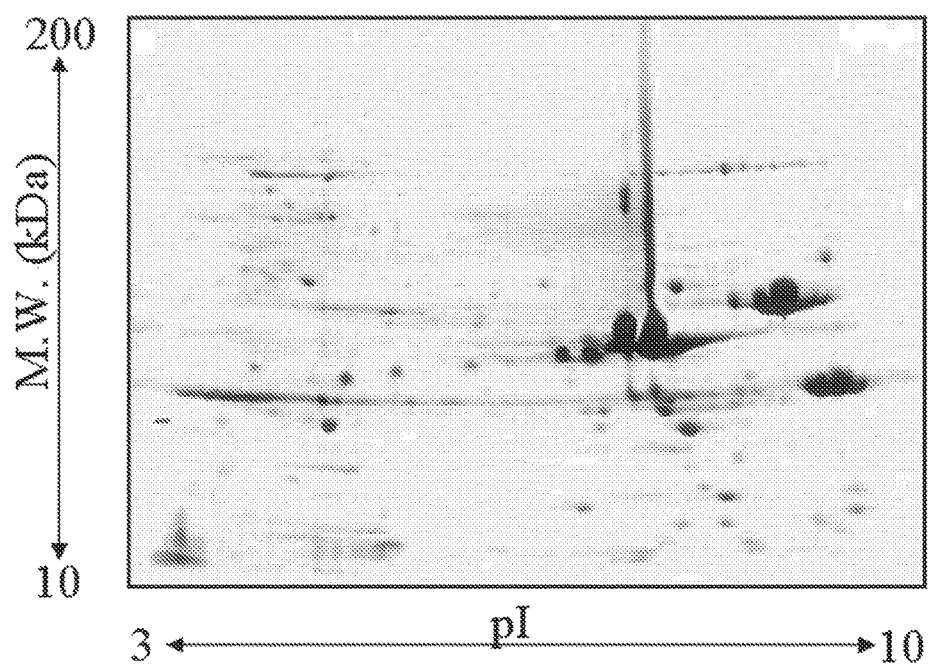
FIG. 1 shows 2D-PAGE of vesicles of the invention.

The amino acid sequence (SEQ ID NO: 1) and nucleotide sequence (SEQ ID NO: 2) are the membrane-bound lync nurein transglyosclyase A (mlta) from the genome sequence of strain MC59 of serogroup B *Neisseria meningitidis*, taken from GenBank accession AAF405041.1 [32]. SEQ ID NO: 3 is NMB0928, SEQ ID NO: 4 is NMB0109, SEQ ID NO: 5 is NMB 1057, SEQ ID NO: 6 is NMB0928$_{new}$, and SEQ ID NO: 8 is NMB1057$_{new}$, which both have shifted start codons.

MODES FOR CARRYING OUT THE INVENTION

Preparation of Meningococcal mltA Knockout Strain

A meningococcal strain was prepared in which the mltA gene is replaced by allelic exchange with an antibiotic cassette.

*N.meningitidis* strain MC58 was transformed with plasmid pBSUDGNA33ERM. This plasmid contains upstream and downstream flanking regions for allelic exchange, a truncated mltA gene, and the ermC gene (encoding erythromycin resistance). The upstream flanking region (including the start codon) from position −867 to +75 and the downstream flanking region (including the stop codon) from position +1268 to +1744 were amplified from MC58 by using the primers U33FOR, U33REV, D33FTOR and D33REV [25]. Fragments were cloned into pBluescript™ and transformed into *E.coli* DH5 by using standard techniques. Once all subcloning was complete, naturally competent *Neisseria* strain MC58 was transformed by selecting a few colonies grown overnight on GC agar plates and mixing them with 20 μl 10 mM Tris-HCl (pH 6.5) containing 1 μg plasmid DNA. The mixture was spotted onto a chocolate agar plate, incubated for 6 h at 37° C. with 5% CO$_2$, and then diluted in phosphate buffered-saline (PBS) and spread on GC agar plates containing 7 μg/ml erythromycin. Allelic exchange with the chromosomal mltA gene was verified by PCR, and lack of MltA expression was confirmed by Western blot analysis.

As reported in reference 25, the mltA knockout strain does not have the correct topological organisation of the cellular membrane, has abnormal cell separation, abnormal cell morphology, undivided septa, double septa, cell clustering, sharing of outer membranes and reduced virulence. Reference 25 also reports that the knockout strain releases various membrane proteins into the culture supernatant, including the PorA, PIB, class 4 and class 5 outer membrane proteins.

A mltA knockout was also made from New Zealand strain 394/98 (lin3; B:4:P1.4), which is the strain from which the MeNZB™ product is produced.

Analysis of Released Proteins

The ΔmltA strain was grown in GC culture medium in a humidified atmosphere containing 5% CO$_2$ until OD$_{600\ nm}$ 0.5. Bacteria were collected by 10 minutes of centrifugation at 3500× g. The supernatant (i.e. culture medium) was filtered through a 0.22 μm pore size filter (Millipore), and the cell-free filtrate was subjected to high-speed centrifugation (200,000× g, 90 min). This centrifugation resulted in formation of a pellet, with about 8-12 mg protein per litre of culture medium. No such pellet was seen if wild-type MC58 bacteria were treated in the same way, and so the pellet formation is a result of the mltA knockout. The pellet was washed twice with PBS (centrifugation 200,000×g, 30 min) for further analysis.

Figure 3A:
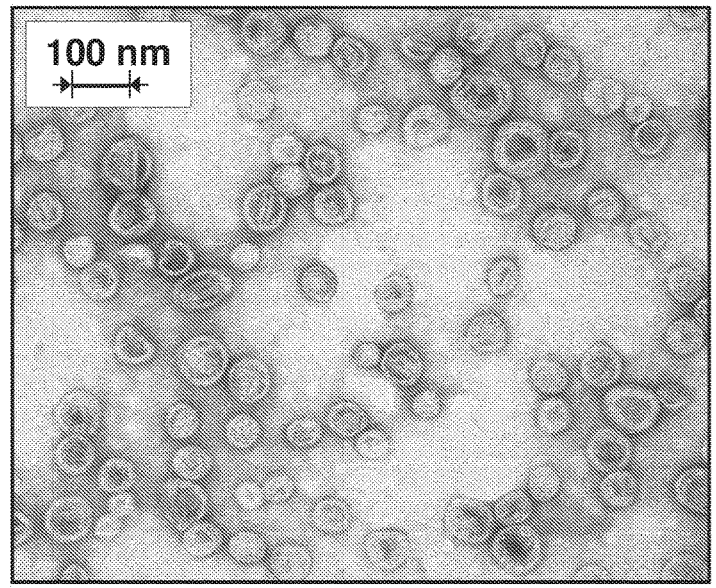
FIGS. 3A-B show electron microscopy of vesicles of the invention.
Figure 3B:
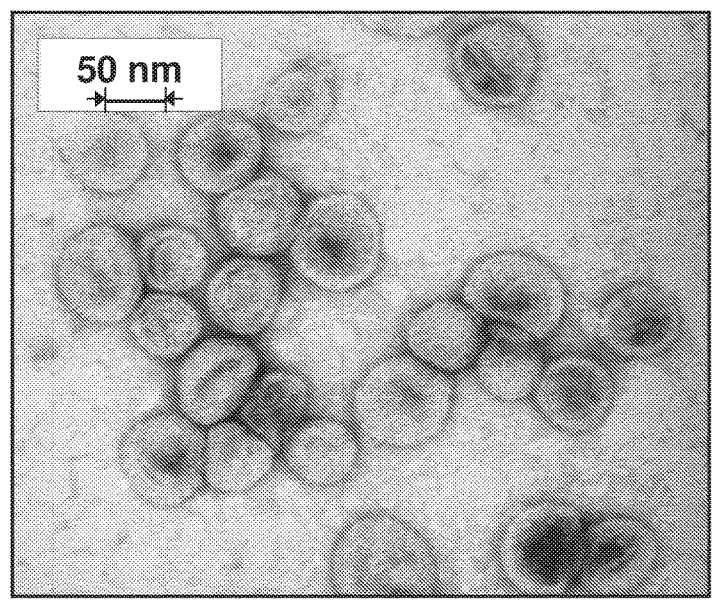

In a first analysis, material from the pellet was re-suspended in PBS and applied to a Superdex 200 PC3.2/30 gel filtration column, run on a SMART system (Amersham Biosciences) that had been equilibrated in PBS. The flow rate was 40 μl/min, and eluate was monitored at 280 nm. The column was calibrated with 20 μg Bleu dextran (2,000 kDa), 10 μg ferritine (440 kDa), 140 μg bovine serum albumin (65 kDa) and 200 μg ribonuclease A (15 kDa). As shown in FIG. 3, most of the proteins eluted in a major peak corresponding to a molecular weight substantially higher than 2,000 kDa. This result suggests that the various proteins are associated.

In a second analysis, the material present in the high molecular weight peak was subjected to negative staining electron microscopy. This analysis revealed the presence of well-organised membrane vesicles with a diameter of about 50-100 nm (FIG. 4).

These experiments suggest that deletion of the mltA gene perturbs the normal assembly of the bacterial membrane, and that this results in the spontaneous release into the culture supernatant of membrane structures which assemble in spherical, homogeneous vesicles.

FIG. 12 shows SDS-PAGE analysis of culture media after growth of wild-type or ΔGNA33 bacteria, and shows the different protein release characteristics.

Analysis of Vesicles

The ΔmltA-derived vesicles were compared to meningococcal vesicles prepared by the 'normal' detergent extraction method.

Meningococcal strains MC58, NZ394/98 and NZ98/254, and their respective isogenic ΔmltA mutants, were grown in 20 ml or 200 ml GC culture medium in humidified atmosphere containing 5% CO$_2$ until OD$_{620\ nm}$ 0.5. Bacteria were collected by 10-minute centrifugation at 3500 g. Vesicles ('DOMVs') were prepared from the wild-type bacteria by detergent extraction as described in reference 206. Vesicles of the invention ('mOMVs') were prepared from knockout strains by filtration through a 0.22 μm pore size filter, followed by high-speed centrifugation (200,000 g, 90 min) of the filtrates, washing of the vesicle-containing pellets (centrifugation 200,000 g, 30 min) twice with phosphate buffer saline, (PBS), and then re-suspension with PBS.

Both the mOMVs and the DOMVs were analysed by denaturing mono-dimensional electrophoresis. Briefly, 20 μg of vesicle proteins were resolved by SDS-PAGE and visualised by Coomassie Blue staining of 12.5% gels. Denaturing (2% SDS) and semi-denaturing (0.2% SDS, no dithiothreitol, no heating) conditions were used mono-dimensional electrophoresis. The amount of protein (20 μg) was determined by DC protein assay (Bio-Rad), using bovine serum albumin as a standard protein.

Figure 2A:
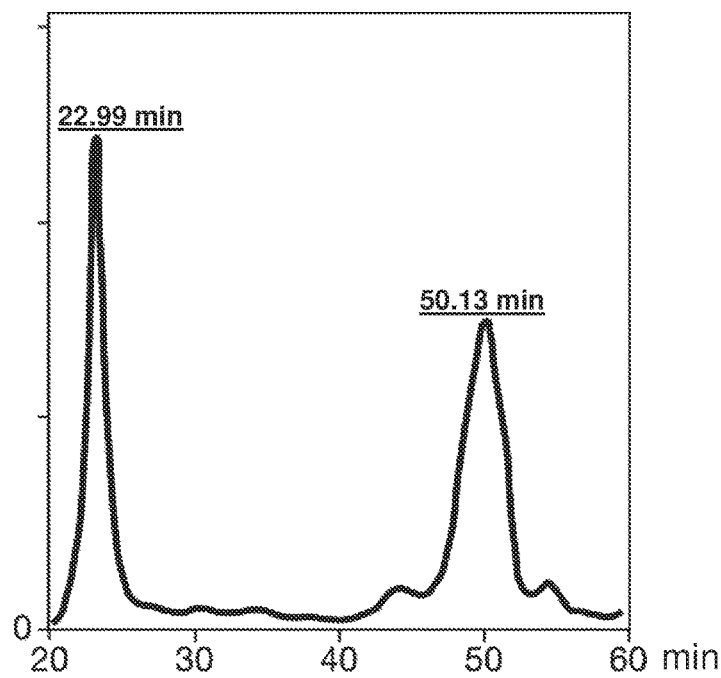
FIGS. 2A-B show the gel filtration outputs with standard proteins (FIG. 2B) and with the centrifugation pellet (FIG. 2A) of the culture supernatant of the ΔmltA strain. They y-axis on both FIG. 2A
Figure 2B:
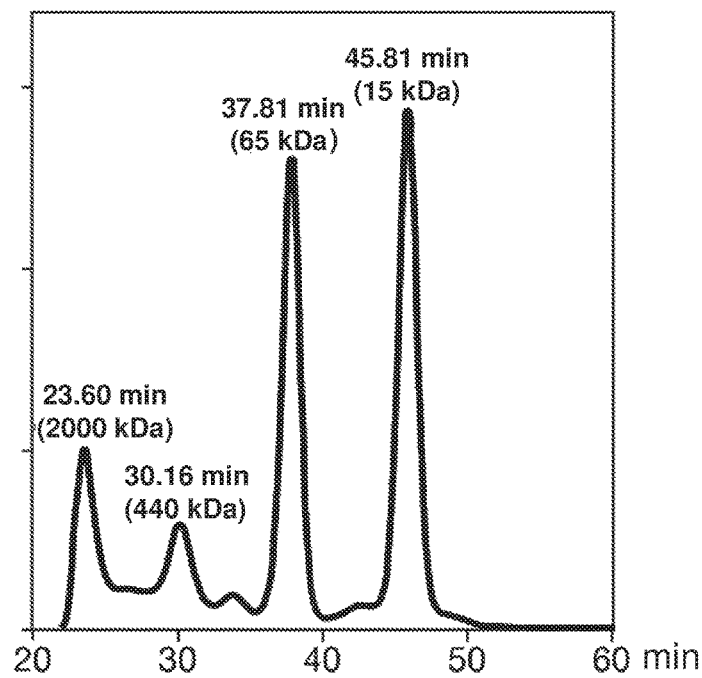

The vesicles were denatured for 3 minutes at 95° C. in SDS-PAGE sample buffer containing 2% SDS. 20 μg of protein were then loaded onto 12.5% acrylamide gels, which were stained with Coomassie Blue R-250. 2-dimensional electrophoresis was also performed on 200 μg of protein brought to a final volume of 125UI with re-swelling buffer containing 7M urea, 2M thiourea, 2% (w/v) (3-((3-cholamidopropyl)dimethylammonio)-1-propane-sulfonate), 65 mM dithiothreitol, 2% (w/v) amidosulfobetain-14, 2 mM tributylphosphine, 20 mM Tris, and 2% (v/v) carrier ampholyte. Proteins were adsorbed overnight onto Immobiline DryStrips (7 cm; pH-gradient 3-10 non linear). Proteins were then 2D-separated. The first dimension was run using a IPGphor Isoelectric Focusing Unit, applying sequentially 150 V for 35 min., 500 V for 35 min., 1,000 V for 30 min, 2,600 V for 10 min., 3,500 V for 15 min., 4,200 V for 15 min., and finally 5,000 V to reach 12 kVh. For the second dimension, the strips were equilibrated and proteins were separated on linear 9-16.5% polyacrylamide gels (1.5-mm thick, 4×7 cm). Gels were again stained with Coomassie Brilliant Blue G-250. 266 protein spots could be seen after Colloidal Coomassie Blue staining (FIG. 2).

The 1D and 2D gels were then subjected to in-gel protein digestion and sample preparation for mass spectrometry analysis. Protein spots were excised from the gels, washed with 100 mM ammonium bicarbonate/acetonitrile 50/50 (V/V), and dried using a SpeedVac centrifuge. Dried spots were digested 2 hours at 37° C. in 12 μl of 0.012 μg/μl sequencing grade trypsin (Promega) in 50 mM ammonium bicarbonate, 5 mM. After digestion, 5 μl of 0.1% trifluoacetic acid was added, and the peptides were desalted and concentrated with ZIP-TIPs (C18, Millipore). Sample were eluted with 2 μl of 5 g/l 2,5-dihydroxybenzoic acid in 50% acetonitrile/0.1% trifluoroacetic acid onto the mass spectrometer Auchorchip 384 (400 μm, Bruker, Bremen, Germany) and allowed to air dry at room temperature. MALDI-TOF spectra were acquired on a Bruker Biflex III MALDI-TOF equipped with a 337 nm $N_2$ laser and a SCOUT 384 multiprobe ion source set in a positive-ion reflector mode. The acceleration and reflector voltages were set at 19 kV and 20 kV, respectively. Typically, each spectrum was determined by averaging 100 laser shots. Spectra were externally calibrated using a combination of four standard peptides, angiotensin II (1,046.54 Da), substance P (1,347.74 Da), Bombensin (1,619.82 Da) and ACTH18-39 Clip human (2,465.20 Da), spotted onto adjacent position to the samples. Protein identification was carried out by both automatic and manual comparison of experimentally-generated monoisotopic values of peptides in the mass range of 700-3000 Da with computer-generated fingerprints using the Mascot software.

Results from the MC58 ΔmltA mutant are shown in FIG. 18. From the 20 excised bands on just the 1D gel, 25 unique proteins were identified, 24 (96%) of which were predicted to be outer-membrane proteins by the PSORT algorithm (Table 1 below). 170 protein spots on the 2D gel, corresponding to 51 unique proteins, were unambiguously identified by MALDI-TOF (Table 1). 44/51 identified proteins have been assigned to the outer membrane compartment by the genome annotation [32]. The 7 remaining proteins were analysed for possible errors in the original annotation. Four proteins (the hypothetical proteins NMB1870, NMB0928 and NMB0109, and the glutamyltranspeptidase NMB1057) could be classified as outer membrane proteins using different start codons from those in ref. 32 e.g. for NMB1870, using the start codon assigned in reference 55.

The combined 1D and 2D electrophoresis experiments identified a total of 65 proteins in the MC58 ΔmltA mutant-derived vesicles. Of these, 6 proteins were identified in both 1D and 2D gels, whereas 14 and 45 were specific for the 1D and 2D gels, respectively (Table 1). Moreover, 61 out of the 65 identified proteins were predicted as membrane-associated proteins by current algorithms, indicating that the ΔmltA vesicles (mOMVs) are mostly, and possible exclusively, constituted by membrane proteins.

The ΔmltA knockout of strain NZ394/98 was similarly subjected to 1D and 2D SDS-PAGE (FIGS. 14 & 15). Table 2 shows 66 proteins that were identified in one or both of the gels, together with the predicted location of the proteins. Again, most of the proteins were predicted as membrane-associated. The 47 proteins common to Tables 1 and 2 are shown in Table 3.

Results from the NZ98/254 ΔmltA mutant are shown in FIG. 19. 66 proteins were identified from these two gels, 57 of which were assigned to the outer membrane compartment. Again, therefore, the mOMVs are highly enriched in outer membrane proteins. 46 of the 57 proteins had also been identified in the MC58-derived mOMVs.

For comparison, FIG. 20 shows the results from NZ98/254 DOMVs. Proteomic analysis revealed 138 proteins, only 44 of which were assigned to the outer membrane compartment. The remaining 94 proteins belonged to the cytoplasmic and inner membrane compartments. Of these 44 membrane proteins, 32 were also found in the 57 outer membrane proteins found in the mOMVs from the isogenic strain.

While mOMVs are largely constituted by outer membrane proteins, therefore, about 70% of DOMV proteins are either cytoplasmic or inner membrane proteins. DOMVs differ from mOMVs not only for the proportion of cytoplasmic proteins but also for the different profile of their outer membrane proteins. Of the 44 outer membrane proteins seen in DOMVs, only 32 were also seen in mOMVs.

19 proteins seen in mOMVs from both MC58 and NZ98/254, but not in the DOMVs from NZ98/254, are listed in Table 4 below.

A total cell extract of bacteria was prepared as follows: Bacterial cells were washed with PBS, and the bacterial pellet was resuspended in 8 ml of 50 mM Tris-HCl pH 7.3 containing protease inhibitor cocktail (Roche Diagnostic). 2 mM EDTA and 2000 units of benzonase (Merck) were added, cells were disrupted at 4° C. with Basic Z 0.75V Model Cell Disrupter equipped with an "one shot head" (Constant System Ltd) by 2 cycles, and the unbroken cells were removed by centrifugation 10 min at 8 000× g at 4° C. This extract was analysed by SDS-PAGE, for comparison with a protein extract of the vesicles produced by ΔGKA33 bacteria. As shown in FIG. 13, the porins PorA and PorB (identities verified by MALDI-TOF sequencing) are seen in the wild-type bacterial outer membrane (lanes 2 & 4) and also in the GNA33 knockout mutant's vesicles (lanes 3 & 5). Moreover, these proteins are retained as stable trimers in the vesicles that do not dissociate into monomers in SDS-PAGE sample buffer with a low concentration of SDS (0.2%) under seminative conditions (no heating before electrophoresis; lanes 2 & 3), but that do denature at 95° C. (lanes 4 & 5).

LPS levels in detergent-extracted OMVs are typically 5-8% by weight, relative to protein [207]. When tested with the Limulus assay, the endotoxin content of the vesicles was about twice as high as found in detergent-extracted OMVs.

Finally, the yield of vesicles in a growing culture was assessed. It was found that up to 20 mg of OMV-associated proteins could be recovered per gram of cells (wet weight) in culture supernatants of early exponentially growing cultures ($OD_{620\,nm}$=0.5).

Vesicle Immunogenicity

As the ΔmltA-derived vesicles are highly enriched in outer membrane proteins, their ability to elicit bactericidal antibodies capable of killing a broad panel of MenB clinical isolates was investigated.

The strain chosen for the testing was 394/98. This strain was chosen because it is the strain from which the MeNZB™ OMV-based vaccine is prepared, thereby aiding a direct comparison of ΔmltA vesicles of the invention with OMVs prepared from the wild-type strain by typical prior art methods.

10 μg of each type of vesicle was adsorbed to an aluminium hydroxide adjuvant (3 mg/ml) and injected into mice 5-week old CD1 female mice (5-10 mice per group). The vesicles were given intraperitoneally on days 0 and 21. Blood samples for analysis were taken on day 34, and were tested for SBA against 15 different serogroup B strains corresponding to 11 different sub-types, including the four major hypervirulent lineages, using pooled baby rabbit serum as the complement source. Serum bactericidal titers were defined as the serum dilution resulting in 50% decrease in colony forming units (CFU) per ml after 60 minutes incubation of bacteria with reaction mixture, compared to control CFU per ml at time 0. Typically, bacteria incubated with the negative control antibody in the presence of complement showed a 150 to 200% increase in CFU/ml during the 60 min incubation. Titers were as follows, expressed as the reciprocal of the serum dilution yielding=50% bacterial killing:

| Serogroup:Type:Subtype | BCA titer | |
|---|---|---|
| | mOMVs | DOMVs |
| B:4:P1.4 | >8192 | >32768 |
| B:15:P1.7, 4 | >65536 | 32768 |
| B:4, 7:P1.7, 4 | >32768 | >32768 |
| B:14:P1.4 | >32768 | >65536 |
| B:4:P1.7, 4 | >32768 | 8192 |
| B:4,:P1.4 | >8192 | >8192 |
| B:14:P1.13 | 16384 | 512 |
| B:4, 7:P1.7, 13 | >8192 | 128 |
| B:4:P1.15 | >8192 | 128 |
| B:21:P1.9 | >8192 | <16 |
| B:2b:P1.10 | 1024 | <16 |
| B:4, 7:P1.19, 15 | 1024 | <16 |
| B:2b:P1.5, 2 | 1024 | <16 |
| B:2a:P1.2 | <16 | <16 |
| B:NT:P1.3 | <16 | <16 |

The results show that serum from ΔmltA-derived vesicles were at least as bactericidally effective, and usually better than, OMVs prepared by chemical extraction, except for the homologous strain. The vesicles of the invention thus give much better cross-strain reactivity than typical OMVs. Moreover, taking a 1:1024 dilution as the threshold for bactericidal efficacy, the vesicles of the invention were effective against 87% of the strains, whereas the artificial OMVs were only 40% effective.

Thus mOMVs are better than DOMVs for eliciting complement-dependent antibody killing when tested over a panel of 15 different serogroup B strains. The anti-mOMV mouse sera showed high bactericidal activities against the homologous strain and against 14 additional strains, including 10 different PorA subtypes. In contrast, mouse sera raised against DOMVs show high bactericidal titers only against six MenB strains, belonging to two PorA subtypes. These results indicate that the protection of anti-mOMV sera was not only due to the elicitation of bactericidal antibodies against PorA, which is one of the most abundant outer membrane proteins and the most potent inducer of bactericidal antibodies, but also to other bactericidal antigens which in mOMVs are present in higher amounts than in DOMVs.

Western Blot

To confirm that the ΔmltA-derived vesicles do contain conserved, protective antigens, they were run on an SDS-PAGE, transferred onto a PDF filter and immunoblotted using specific anti-sera against six proteins antigens previously shown to be protective and highly conserved, including '287', '953', '741' (GNA1870) and 'NadA'.

The vesicles were separated onto 10% acrylamide SDS-PAGE gels employing a Mini-Protean II electrophoresis apparatus (Bio-Rad). After protein separation, gels were equilibrated with 48 mM Tris-HCl, 39 mM glycine, pH 9.0, 20% (v/v) methanol and transferred to a nitrocellulose membrane (Bio-Rad) using a Trans-Blot™ semi-dry electrophoretic transfer cell. The nitrocellulose membranes were blocked with 10% (w/v) skimmed milk in PBS containing 0.2% (w/v) sodium azide.

Figure 5:
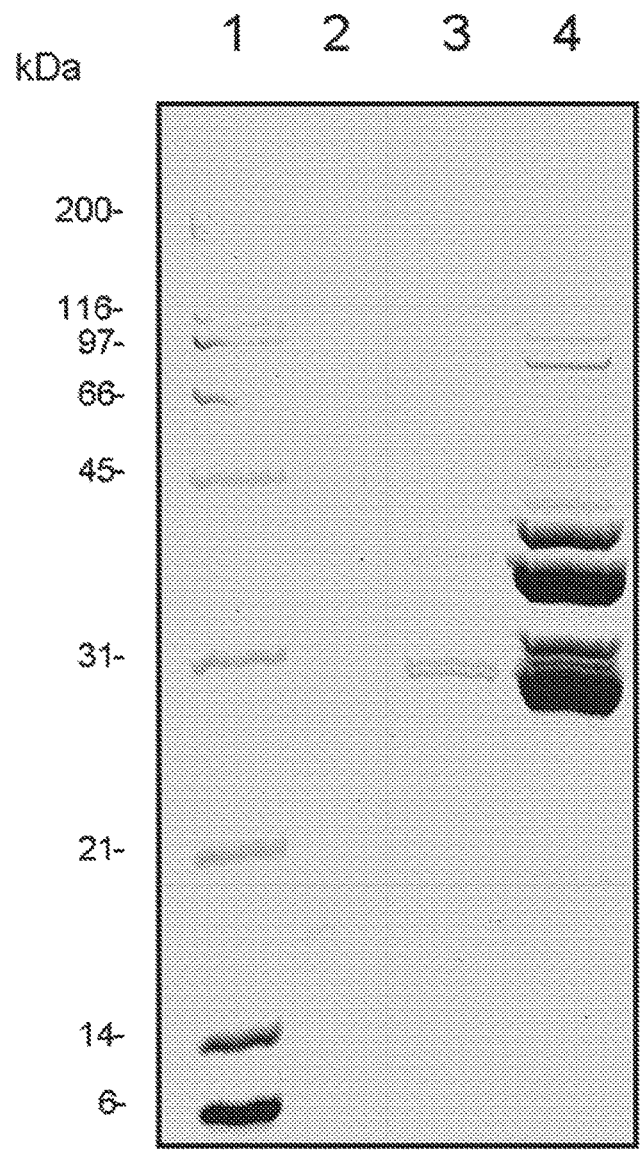
FIG. 5 compares the proteins released into culture supernatants by wild-type or ΔGNA33 bacteria. Lane 1: Molecular weight markers; lane 2: culture medium control; lane 3: 20 μg proteins collected by high speed centrifugation of ΔGNA33 culture medium at OD$_{620\ nm}$=0.5, corresponding to 6.5 ml of culture medium; lane 4: proteins collected by high speed centrifugation from 6.5 ml of wild-type MC58 culture medium at OD$_{620\ nm}$=0.5.
Figure 6:
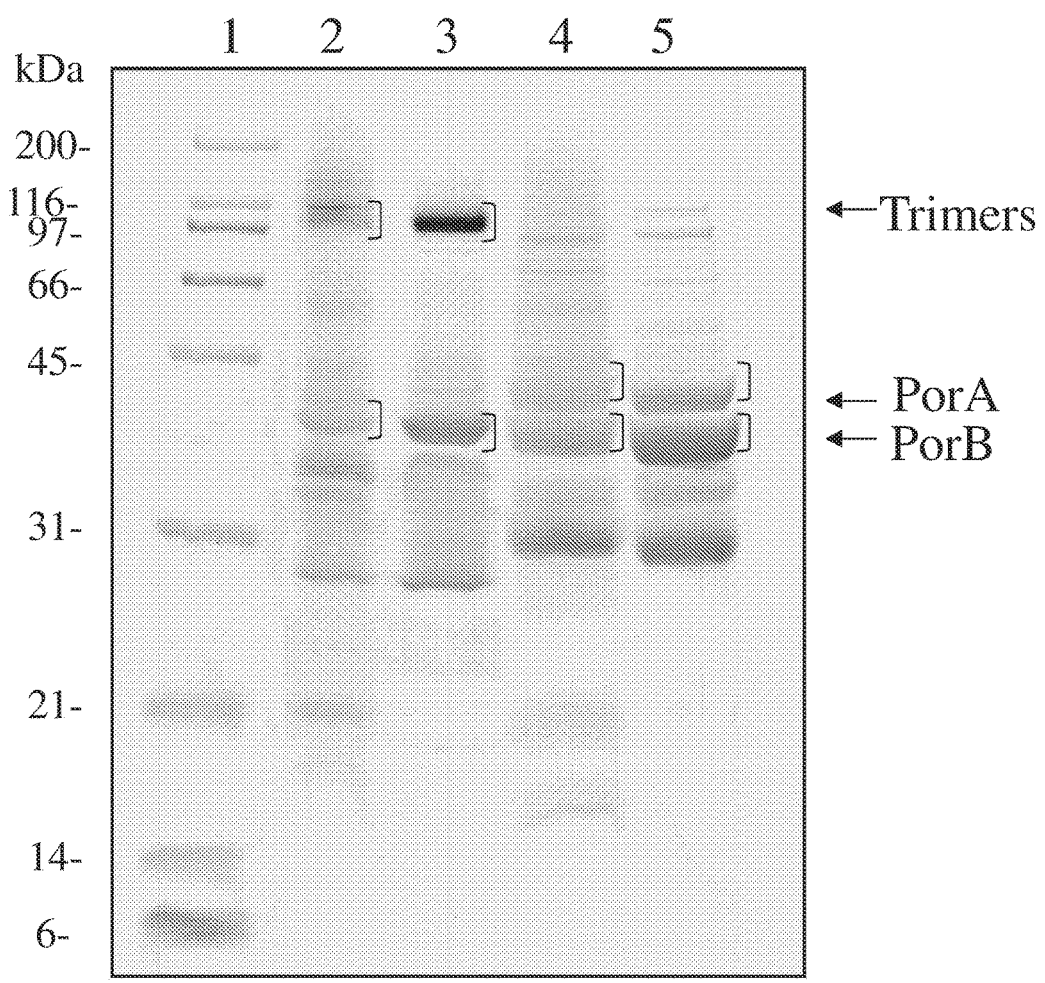
FIG. 6 shows SDS-PAGE of a wild-type MC58 total extract (lanes 2 and 4) and of vesicles released by ΔGNA33 knockout mutant (lanes 3 and 5). Lanes 2 and 3 are proteins not denatured at 95° C. prior to SDS-PAGE; lanes 4 and 5 were denatured at 95° C.
Figure 7A:
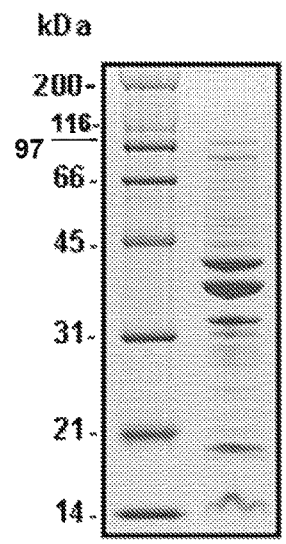
FIGS. 7A-B show 1D SDS-PAGE (FIG. 7A) and 2D SDS-PAGE (FIG. 7B) of vesicles prepared from strain 394/98.
Figure 7B:
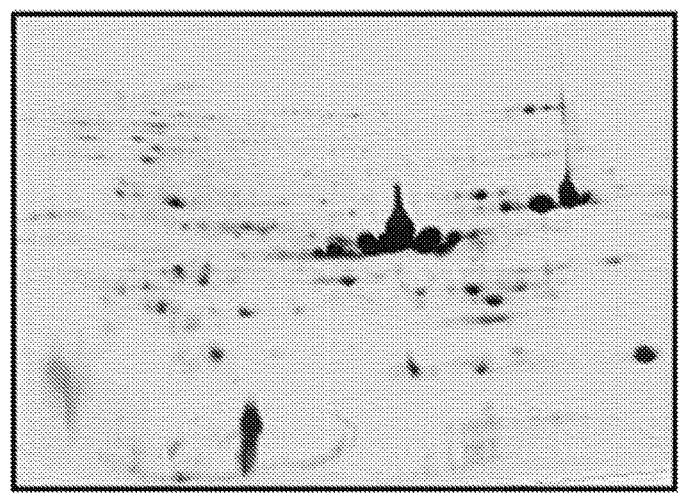
Figure 8A:
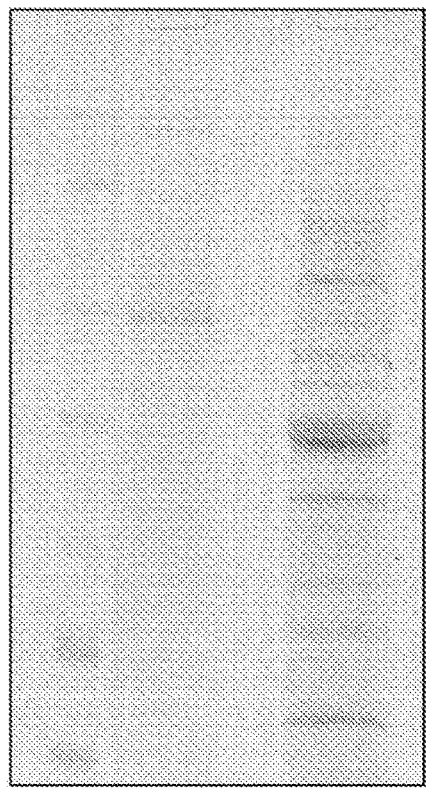
FIGS. 8A-B show 1D SDS-PAGE of vesicles prepared from tolR ExPEC knockout strains.
Figure 8B:
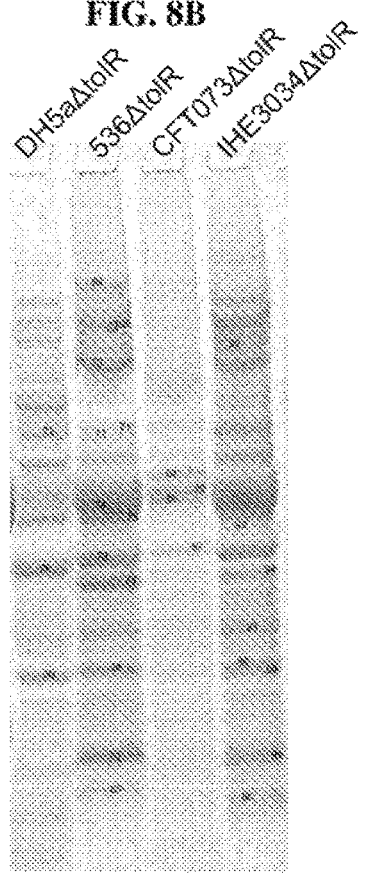
Figure 9A:
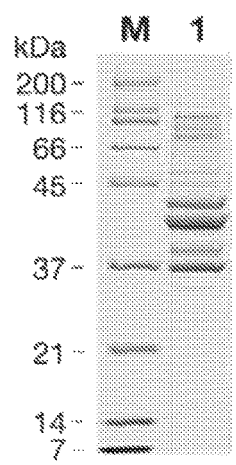
FIGS. 9A-D show 1D SDS-PAGE (FIGS. 9A and 9C) and 2D SDS-PAGE (FIGS. 9B and 9D) of vesicles from ΔmltA knockout meningococci.
Figure 9B:
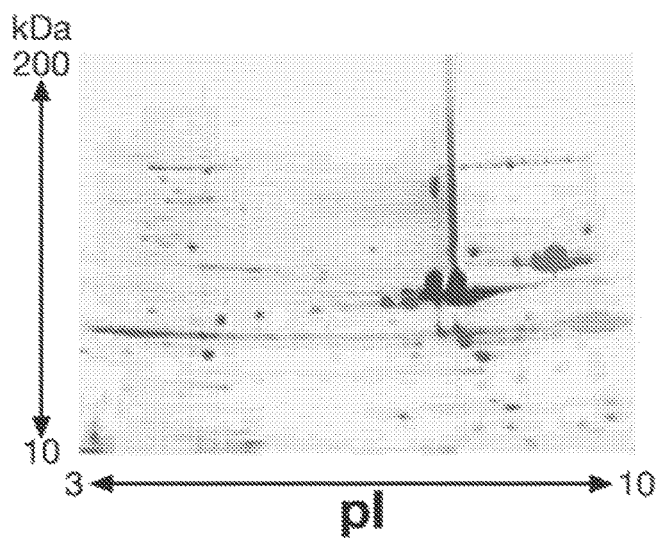
Figure 9C:
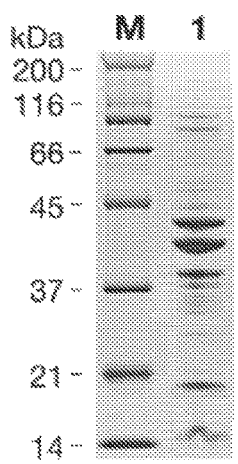
Figure 9D:
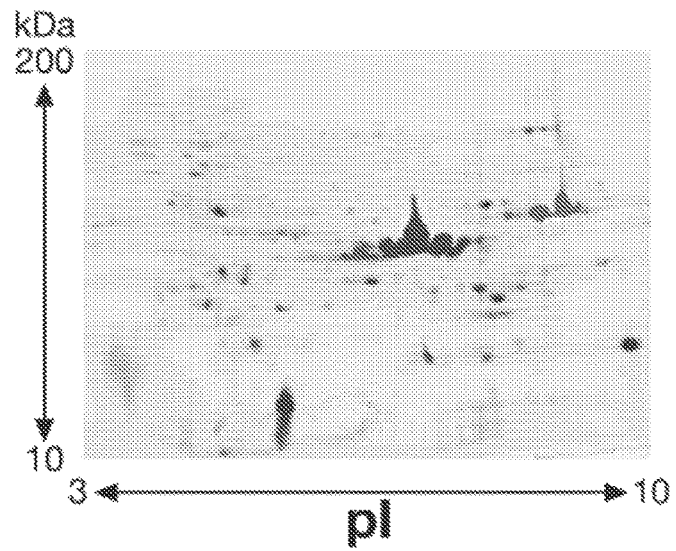

As shown in FIG. 5, all six proteins were abundant in the vesicles. In contrast, the same six proteins were poorly represented in the DOMVs.

In conclusion, the ΔmltA-derived vesicles are predominantly constituted by outer membrane proteins, whereas DOMVs are heavily contaminated by cytoplasmic proteins. When used to immunize mice, sera raised against ΔmltA-derived vesicles showed a higher and wider strain coverage than DOMVs.

Extraintestinal Pathogenic *E.coli*

A knockout strain of ExPEC CFT073 was prepared by isogenic deletion of the tolR gene, replacing it with a kanamycin resistance marker. The knockout strain was grown to $OD_{600\,nm}$ 0.4, and the culture was then centrifuged. The supernatant was filtered through a 0.22 μm filter and the filtrate was precipitated using TCA. The pellet was then resuspended in Tris buffer.

The same growth and purification procedure was used for the parent strain, without the knockout, and SDS-PAGE analysis of the two final preparations is shown in FIG. 16. The right-hand band is from the knockout strain and shows enrichment of several protein bands.

Further tolR knockout ExPEC strains were prepared from strains DH5a, 536 and IHE3034. Vesicles were prepared as before, and SDS-PAGE analysis of TCA precipitates is shown in FIG. 17.

The knockout mutant produces high amounts of vesicles, and these vesicles were subjected to proteomic analyses, including 1D and 2D SDS-PAGE and tryptic digestion of surface-exposed proteins in the vesicles followed by sequence analysis of released peptides.

It will be understood that the invention has been described by way of example only and modifications may be made whilst remaining within the scope and spirit of the invention.

TABLE 1

| | NMB | Protein name/theoretical MW/theoretical pI/gravy index | 1 d | 3-10 | Psort |
|---|---|---|---|---|---|
| 1 | NMB0018 | pilin PilE/15 246/9.21/−0.571 | X | | OM-PS |
| 2 | NMB0035 | conserved hypothetical protein/40 218/4.74/−0.371 | | X | OM-IN |
| 3 | NMB0044 | peptide methionine sulfoxide reductase/55 718/6.54/−0.569 | | X | OM-IN |
| 4 | NMB0086 | hypothetical protein/34 987/4.82/−0.505 | | X | OM-IN |
| 5 | NMB0088 | outer membrane protein P1, putative/45 902/9.35/−0.428 | X | | OM-PS |
| 6 | NMB0109 | conserved hypothetical protein/43 188/6.77/−0.587 | X | X | OM-PS(b) |
| 7 | NMB0124 | translation elongation factor TU/42 909/5.07/−0.136 | | X | cyto |
| | NMB0139 | translation elongation factor TU/42 925/5.07/−0.142 | | | cyto |
| 8 | NMB0138 | elongation factor G (EF-G)/77 244/5.08/−0.293 | | X | cyto |
| 9 | NMB0181 | outer membrane protein OmpH, putative/16 829/9.07/−0.897 | X | | OM-PS |
| 10 | NMB0182 | outer membrane protein Omp85/86 254/8.37/−0.505 | X | X | OM-PS |
| 11 | NMB0204 | lipoprotein, putative/12 207/8.08/−0.446 | X | | OM-PS |
| 12 | NMB0278 | thiol: disulfide interchange protein DsbA/23 428/5.16/−0.298 | | X | OM-IN |
| 13 | NMB0281 | peptidyl-prolyl cis-trans isomerase/35 248/9.62/−0.388 | | X | OM-IN |
| 14 | NMB0294 | thiol: disulfide interchange protein DsbA/23 566/5.09/−0.477 | | X | OM-IN |
| 15 | NMB0313 | lipoprotein, putative/52 645/9.97/−0.824 | X | | OM-PS |
| 16 | NMB0345 | cell-binding factor, putative/29 448/9.13/−0.570 | X | X | OM-PS |
| 17 | NMB0346 | hypothetical protein/26439/5.15/−0.716 | | X | OM-PS |
| 18 | NMB0382 | outer membrane protein class 4/23 969/6.26/−0.456 | X | X | OM-PS |
| 19 | NMB0407 | thiol: disulfide interchange protein DsbA/21 721/9.23/−0.308 | | X | OM-PS |
| 20 | NMB0460 | transferrin-binding protein 2/75 292/5.79/−0.982 | X | | OM-IN |
| 21 | NMB0461 | transferrin-binding protein 1/99 314/9.45/−0.699 | X | | OM-PS |
| 22 | NMB0550 | thiol: disulfide interchange protein DsbC/26 451/6.93/−0.345 | | X | OM-IN |
| 23 | NMB0554 | dnaK protein/68 792/4.85/−0.357 | | X | cyto |
| 24 | NMB0622 | outer membrane lipoprotein carrier protein/19 996/9.47/−0.490 | | X | OM-PS |
| 25 | NMB0623 | spermidine/putrescine ABC transporter/39 511/5.38/−0.437 | | X | OM-PS |
| 26 | NMB0634 | iron(III) ABC transporter, periplasmic binding protein/35 806/9.60/−0.338 | | X | OM-PS |
| 27 | NMB0663 | outer membrane protein NsgA/16 563/9.49/−0.214 | X | | OM-PS |
| 28 | NMB0700 | IgA-specific serine endopeptidase | | X | OM-PS |
| 29 | NMB0703 | competence lipoprotein ComL/29 275/8.72/−0.761 | | X | OM-IN |
| 30 | NMB0783 | conserved hypothetical protein/15 029/7.05/−0.221 | | X | OM-PS |
| 31 | NMB0787 | amino acid ABC transporter/26 995/5.42/−0.287 | | X | OM-IN |
| 32 | NMB0873 | outer membrane lipoprotein LolB, putative/19 575/5.23/−0.470 | | X | OM-IN |
| 33 | NMB0928 | hypothetical protein/39 502/9.13/−0.596 | X | X | OM-IN(b) |
| 34 | NMB1030 | conserved hypothetical protein/18 700/7.16/−0.429 | | X | OM-PS |
| 35 | NMB1053 | class 5 outer membrane protein/28 009/9.68/−0.610 | X | X | OM-PS |
| 36 | NMB1057 | gamma-glutamyltranspeptidase/61 590/5.94/−0.160 | | X | OM-IN(b) |
| 37 | NMB1126 | hypothetical protein/22 025/8.03/−0.355 | X | X | OM-IN |
| | NMB1164 | hypothetical protein/22 025/8.03/−0.355 | | | OM-IN |
| 38 | NMB1285 | enolase/46 134/4.78/−0.200 | | X | cyto |
| 39 | NMB1301 | 30S ribosomal protein S1/61 177/4.9/−0.240 | | X | cyto |
| 40 | NMB1332 | carboxy-terminal peptidase/53 238/9.12/−0.420 | X | | IN |
| 41 | NMB1352 | hypothetical protein/13 699/9.52/−1.397 | X | | OM-PS |
| 42 | NMB1429 | outer membrane protein PorA/40.129/8.73 | X | X | OM-PS |
| 43 | NMB1457 | transketolase/71 659/5.45/−0.183 | | X | cyto |
| 44 | NMB1483 | lipoprotein NlpD, putative/40 947/9.55/−0.266 | X | X | OM-PS |
| 45 | NMB1533 | H.8 outer membrane protein/18 886/4.61/17 | | X | OM-IN |
| 46 | NMB1557 | conserved hypothetical protein/15 419/7.34/−0.429 | | X | OM-PS |
| 47 | NMB1567 | macrophage infectivity/potentiator/26 875/5.50/−0.540 | | X | OM-IN |
| 48 | NMB1578 | conserved hypothetical protein/21 135/4.86/−0.381 | | X | OM-IN |
| 49 | NMB1612 | amino acid ABC transporter/27 970/4.87/−0.408 | | X | OM-PS |
| 50 | NMB1636 | opacity protein: authentic frameshift/27180/9.52 | X | X | OM-PS |
| 51 | NMB1710 | glutamate dehydrogenase, NADP-specific/48 490/5.98/−0.190 | | X | cyto |
| 52 | NMB1714 | multidrug efflux pump channel protein/48 482/8.38/−0.261 | | X | OM |
| 53 | NMB1870 | hypothetical protein/26 964/7.23/−0.485 | | X | OM-IN(b) |
| 54 | NMB1898 | lipoprotein/17 155/7.01/−0.709 | | X | OM-IN |
| 55 | NMB1946 | outer membrane lipoprotein/29 258/5.01/−0354 | | X | OM |
| 56 | NMB1949 | soluble lytic murein transglycosylase; putative/65 617/9.31/−0.525 | X | | OM-IN |
| 57 | NMB1961 | VacJ-related protein/27.299/4.65/−0.344 | | X | OM-PS |
| 58 | NMB1969 © | serotype-1-specific antigen, putative | | X | cyto |
| 59 | NMB1972 | chaperonin, 60 kDa/57 423/4.9/−0.052 | | X | cyto |
| 60 | NMB1988 | Iron-regulated outer membrane protein FrpB/76 823/9.42/−0.700 | X | | OM-PS |
| 61 | NMB2039 | major outer membrane protein PIB/33 786/6.54/−0.468 | X | X | OM-PS |
| 62 | NMB2091 | hemolysin, putative/19 412/9.55/−0.152 | X | | OM-IN |
| 63 | NMB2095 | adhesin complex protein, putative/11 385/9.52/−0.470 | X | | OM-IN |
| 64 | NMB2102 | elongation factor TS (EF-TS)/30 330/5.30/−0.016 | | X | cyto |
| 65 | NMB2159 | glyceraldehyde 3-phosphate dehydrogenase/35 845/5.40/−0.028 | | X | cyto |

TABLE 2

| | NMB | ANNOTATION | PSORT | 1 D | 2 D |
|---|---|---|---|---|---|
| 1 | NMB0035 | conserved hypothetical protein | OM-IM | | X |
| 2 | NMB0044 | peptide methionine sulfoxide reductase | OM-IM | | X |
| 3 | NMB0086 | hypothetical protein | OM-IM | | X |

TABLE 2-continued

| | NMB | ANNOTATION | PSORT | 1 D | 2 D |
|---|---|---|---|---|---|
| 4 | NMB0088 | outer membrane protein P1, putative | OM-PS | X | X |
| 5 | NMB0109 | conserved hypothetical protein | OM-PS(b) | X | X |
| 6 | NMB0124 | | cyto(c, x) | X | X |
| 7 | NMB0138 | elongation factor G (EF-G) | cyto (x) | | X |
| 8 | NMB0182 | outer membrane protein Omp85 | OM-PS | X | X |
| 9 | NMB0204 | lipoprotein, putative | OM-PS | | X |
| 10 | NMB0278 | thiol: disulfide Interchange protein DsbA | OM-IM | | X |
| 11 | NMB0294 | thiol: disulfide Interchange protein DsbA | OM-IM | | X |
| 12 | NMB0313 | lipoprotein, putative | OM | X | |
| 13 | NMB0345 | cell-binding factor, putative | OM-PS | X | X |
| 14 | NMB0346 | hypothetical protein | OM-PS | X | X |
| 15 | NMB0382 | outer membrane protein class 4 | OM-PS | X | X |
| 16 | NMB0460 | transferrin-binding protein 2 | OM-IM | | X |
| 17 | NMB0461 | transferrin-binding protein 1 | OM-PS | X | |
| 18 | NMB0462 | spermidine/putrescine ABC transporter, periplasmic spermidine/putrescine-binding protein | OM-PS(b) | | X |
| 19 | NMB0550 | thiol: disulfide interchange protein DsbC | OM-IM | X | X |
| 20 | NMB0554 | dnaK protein | LITT. | | X |
| 21 | NMB0604 | alcohol dehydrogenase, zinc-containing | IM | | X |
| 22 | NMB0623 | spermidine/putrescine ABC transporter, periplasmic spermidine/putrescine-binding protein | OM-IM | | X |
| 23 | NMB0631 | phosphate acetyltransferase Pta | IM | | X |
| 24 | NMB0634 | iron(III) ABC transporter, periplasmic binding protein | OM-PS | | X |
| 25 | NMB0663 | outer membrane protein NspA | OM-PS | X | X |
| 26 | NMB0669 | conserved hypothetical protein | OM-PS | X | |
| 27 | NMB0703 | competence lipoprotein ComL comL | OM-IM | X | X |
| 28 | NMB0787 | amino acid ABC transporter, periplasmic amino acid-binding protein | OM | X | |
| 29 | NMB0872 | conserved hypothetical protein | OM-PS | X | |
| 30 | NMB0873 | outer membrane lipoprotein LolB, putative | OM-IM | X | X |
| 31 | NMB0928 | hypothetical protein | OM-IM(b) | X | X |
| 32 | NMB0944 | 5-methyltetrahydropteroyltriglutamate-homocysteine methyltransferase | IM | | X |
| 33 | NMB0983 | phosphoribosylaminolNidazolecarboxamide formyltransferase/INP cyclohydrolase | IM | | X |
| 34 | NMB1030 | conserved hypothetical protein | OM-PS | X | X |
| 35 | NMB1040 | hypothetical protein | OM-PS | X | |
| 36 | NMB1053 | class 5 outer membrane protein opc | OM-PS | X | X |
| 37 | NMB1057 | gamma-glutamyltranspeptidase | OM-IM(b) | | X |
| 38 | NMB1124 | hypothetical protein | OM-IM | X | |
| 39 | NMB1125 | hypothetical protein | OM-IM | X | X |
| 40 | NMB1126 | hypothetical protein | OM-IM | X | X |
| 41 | NMB1285 | Enolase | LITT. | | X |
| 42 | NMB1301 | 30S ribosomal protein S1 | LITT. | | X |
| 43 | NMB1309 | Nbrial biogenesis and twitching motility protein, putative | IM | X | X |
| 44 | NMB1313 | trigger factor | FACS+ | | X |
| 45 | NMB1332 | carboxy-terminal peptidase | IM | X | X |
| 46 | NMB1398 | Cu—Zn-superoxide dismutase | OM-PS | | X |
| 47 | NMB1429 | outer membrane protein PorA porA | OM-PS | X | X |
| 48 | NMB1483 | lipoprotein NlpD | OM-PS | X | X |
| 49 | NMB1497 | TonB-dependent receptor | OM | X | |
| 50 | NMB1518 | acetate kinase | IM | | X |
| 51 | NMB1533 | H.8 outer membrane protein | OM-PS | | X |
| 52 | NMB1567 | macrophage infectivity potentiator | OM-IM | | X |
| 53 | NMB1574 | ketol-acid reductoisomerase | CYTO | | X |
| 54 | NMB1612 | amino acid ABC transporter, periplasmic amino acid-binding protein | OM-IM | | X |
| 55 | NMB1710 | glutamate dehydrogenase, NADP-specific | LITT. | | X |
| 56 | NMB1812 | putative, pilQ protein, authentic frameshift | OM-PS | | X |
| 57 | NMB1870 | hypothetical protein | OM-IM(b) | | X |
| 58 | NMB1898 | lipoprotein mlp | OM-IM | X | X |
| 59 | NM81902 | DNA polymerase III, beta subunit | CYTO | | X |
| 60 | NMB1949 | soluble lytic murein transglycosylase, putative | OM-IM | X | |
| 61 | NMB1961 | VacJ-related-protein | OM-PS | | X |
| 62 | NMB1972 | chaperonin, 60 kDa | LITT. | X | X |
| 63 | NMB1988 | iron-regulated outer membrane protein FrpB | OM-PS | X | X |
| 64 | NMB2039 | major outer membrane protein PIB | OM-PS | X | X |
| 65 | NMB2091 | hemolysin, putative | OM-IM | X | |
| 66 | NMB2139 | conserved hypothetical protein | OM-IM | | X |
| | | | | 34 | 56 |

TABLE 3

| | | | | | | | |
|---|---|---|---|---|---|---|---|
| NMB0035 | NMB0044 | NMB0086 | NMB0088 | NMB0109 | NMB0124 | NMB0138 | NMB0182 |
| NMB0204 | NMB0278 | NMB0294 | NMB0313 | NMB0345 | NMB0346 | NMB0382 | NMB0460 |
| NMB0461 | NMB0550 | NMB0554 | NMB0623 | NMB0634 | NMB0663 | NMB0703 | NMB0787 |
| NMB0873 | NMB0928 | NMB1030 | NMB1053 | NMB1057 | NMB1126 | NMB1285 | NMB1301 |
| NMB1332 | NMB1429 | NMB1483 | NMB1533 | NMB1567 | NMB1612 | NMB1710 | NMB1870 |
| NMB1898 | NMB1949 | NMB1961 | NMB1972 | NMB1988 | NMB2039 | NMB2091 | |

TABLE 4

| | | | | | | |
|---|---|---|---|---|---|---|
| NMB0044 | NMB0086 | NMB0204 | NMB0278 | NMB0294 | NMB0313 | NMB0345 |
| NMB0346 | NMB0460 | NMB0550 | NMB0873 | NMB0928 | NMB1030 | NMB1057 |
| NMB1483 | NMB1870 | NMB1898 | NMB1961 | NMB2091 | | |

REFERENCES

The Contents of Which are Hereby Incorporated by Reference

[1] Bjune et al. (1991) Lancet 338(8775):1093-1096.
[2] de Kleijn et al. (2001) Vaccine 20:352-358.
[3] U.S. Pat. Nos. 5,597,572 & 5,747,653; see also European patent 0301992.
[4] European patent 0449958 (granted from WO90/06696).
[5] U.S. Pat. No. 5,705,161; see also WO94/08021.
[6] WO01/91788.
[7] Parmar et al. (1997) Vaccine 15:1641-1651.
[8] WO99/59625.
[9] WO00/50074.
[10] U.S. Pat. Nos. 5,552,146, 5,981,213 & 5,993,826; see also WO93/03761.
[11] Zhou et al. (1998) FEMS Microbiol Lett 163:223-228.
[12] Kadurugamuwa & Beveridge (1999) Microbiology 145:2051-2060.
[13] WO97/05899.
[14] Kesavalu et al. (1992) Infect. Immun. 60:1455-1464.
[15] Blanco et al. (1999) J Immunol 163:2741-2746.
[16] WO01/09350.
[17] Keenan et al. (1998) FEMS Microbiol Lett 161:21-27.
[18] WO00/25811.
[19] WO01/52885.
[20] WO98/56901.
[21] WO02/09746.
[22] WO02/062378.
[23] WO2004/014417.
[24] WO2004/019977.
[25] Ada-Bobie et al. (2004) Infect Immun 72:1914-1919.
[26] Jennings et al. (2002) Eur J Biochem 269:3722-3731.
[27] Pollard & Moxon (2002) Arch Dis Child 87:13-17.
[28] WO2004/014417.
[29] Shockman & Höltje (1994) Microbial peptidoglycan (murein) hydrolases. Pages 131-166 in Bacterial Cell Wall (eds. Ghuysen & Hakenbeck).
[30] WO00/66741.
[31] Parkhill et al. (2000) Nature 404:502-506.
[32] Tettelin et al. (2000) Science 287:1809-1815.
[33] Maiden et al. (1998) PNAS USA 95:3140-3145.
[34] WO99/10497.
[35] Steeghs et al. (2001) The EMBO Journal 20:6937-6945.
[36] WO02/07763.
[37] European patent 0624376.
[38] Claassen et al. (1996) Vaccine 14:1001-1008.
[39] Peeters et al. (1996) Vaccine 14:1009-1015.
[40] van der Ley et al. (1995) Vaccine 13:401-7.
[41] WO2004/048404.
[42] WO 02/062378.
[43] WO 2004/014417.
[44] UK patent application 0419627.5.
[45] Russo & Johnson (2000) J Infect Dis 181:1753-4.
[46] Bernadac et al. (1998) J Bacterial 180(18):4872-8.
[47] WO02/09643.
[48] Beveridge (1999) J Bacterial 181:4725-33.
[49] Moe et al. (2002) Infect Immun 70:6021-31.
[50] Arigita et al. (2003) Vaccine 21:950-960.
[51] WO2004/046177
[52] U.S. Pat. No. 6,180,111.
[53] WO01/34642.
[54] Maiden et al. (1998) PNAS USA 95:3140-3145.
[55] Masignani et al. (2003) J Exp Med 197:789-799.
[56] WO03/063766.
[57] Fletcher et al. (2004) Infect Immun 72:2088-2100.
[58] Zhu et al. (2000) J Bacterial 182:439-47.
[59] Moe et al. (2001) Infect Immun 69:3762-71.
[60] Seib et al. (2003) FEBS Lett 546:411-5.
[61] WO01/64922
[62] Gennaro (2000) Remington: The Science and Practice of Pharmacy. 20th edition, ISBN: 0683306472.
[63] RIVM report 124001 004.
[64] Katial et al. (2002) Infect Immun 70:702-7.
[65] RIVM report 000012 003.
[66] WO03/009869.
[67] Almeida & Alpar (1996) J. Drug Targeting 3:455-467.
[68] Agarwal & Mishra (1999) Indian J Exp Biol 37:6-16.
[69] Vaccine Design . . . (1995) eds. Powell & Newman. ISBN: 030644867X. Plenum.
[70] WO00/23105.
[71] WO90/14837.
[72] U.S. Pat. No. 5,057,540.
[73] WO96/33739.
[74] EP-A-0109942.
[75] WO96/11711.
[76] WO00/07621.
[77] Barr et al. (1998) Advanced Drug Delivery Reviews 32:247-271.
[78] Sjolanderet et al. (1998) Advanced Drug Delivery Reviews 32:321-338.
[79] Niikura et al. (2002) Virology 293:273-280.
[80] Lenz et al. (2001) J Immunol 166:5346-5355.
[81] Pinto et al. (2003) J Infect Dis 188:327-338.
[82] Gerber et al. (2001) Virol 75:4752-4760.
[83] WO03/024480
[84] WO03/024481
[85] Gluck et al. (2002) Vaccine 20:B10-B16.
[86] EP-A-0689454.
[87] Johnson et al. (1999) Bioorg Med Chem Lett 9:2273-2278.
[88] Evans et al. (2003) Expert Rev Vaccines 2:219-229.
[89] Meraldi et al. (2003) Vaccine 21:2485-2491.
[90] Pajak et al. (2003) Vaccine 21:836-842.
[91] Kandimalla et al. (2003) Nucleic Acids Research 31:2393-2400.
[92] WO02/26757.
[93] WO99/62923.
[94] Krieg (2003) Nature Medicine 9:831-835.
[95] McCluske et al. (2002) FEMS Immunology and Medical Microbiology 32:179-185.
[96] WO98/40100.
[97] U.S. Pat. No. 6,207,646.
[98] U.S. Pat. No. 6,239,116.
[99] U.S. Pat. No. 6,429,199.
[100] Kandimalla et al. (2003) Biochemical Society Transactions 31 (part 3):654-658.
[101] Blackwell et al. (2003) J Immunol 170:4061-4068.
[102] Krieg (2002) Trends Immunol 23:64-65.

[103] WO01/95935.
[104] Kandimalla et al. (2003) *BBRC* 306:948-953.
[105] Bhagat et al. (2003) *BBRC* 300:853-861.
[106] WO03/035836.
[107] WO95/17211.
[108] WO98/42375.
[109] Beignon et al. (2002) *Infect Immun* 70:3012-3019.
[110] Pizza et al. (2001) *Vaccine* 19:2534-2541.
[111] Pizza et al. (2000) *Int J Med Microbiol* 290:455-461.
[112] Scharton-Kersten et al. (2000) *Infect Immun* 68:5306-5313.
[113] Ryan et al. (1999) *Infect Immun* 67:6270-6280.
[114] Partidos et al. (1999) *Immunol Lett* 67:209-216.
[115] Peppoloni et al. (2003) *Expert Rev Vaccines* 2:285-293.
[116] Pine et al. (2002) *J Control Release* 85:263-270.
[117] Domenighini et al. (1995) *Mol Microbiol* 15:1165-1167.
[118] WO99/40936.
[119] WO99/44636.
[120] Singh et al] (2001) *J Cont Release* 70:267-276.
[121] WO99/27960.
[122] U.S. Pat. No. 6,090,406
[123] U.S. Pat. No. 5,916,588
[124] EP-A-0626169.
[125] WO99/52549.
[126] WO01/21207.
[127] WO01/21152.
[128] Andrianov et al. (1998) *Biomaterials* 19:109-115.
[129] Payne et al. (1998) *Adv Drug Delivery Review* 31:185-196.
[130] Stanley (2002) *Clin Exp Dermatol* 21:571-517.
[131] Jones (2003) *Curr Opin Investig Drugs* 4:214-218.
[132] WO99/11241.
[133] WO94/00153.
[134] WO98/57659.
[135] European patent applications 0835318,0735898 and 0761231.
[136] Bakke et al. (2001) *Infect. Immun.* 69:5010-5015.
[137] WO01/30390.
[138] http://neisseria.org/nm/typing/mlst/
[139] Pettersson et al. (1994) *Microb Pathog* 17(6):395-408.
[140] Welsch et al. (2002) Thirteenth International Pathogenic Neisseria Conference, Norwegian Institute of Public Health, Oslo, Norway; Sep. 1-6, 2002. *Genome-derived antigen (GNA) 2132 elicits protective serum antibodies to groups B and C Neisseria meningitidis strains.*
[141] Santos et al. (2002) Thirteenth International Pathogenic Neisseria Conference, Norwegian Institute of Public Health, Oslo, Norway; Sep. 1-6, 2002. *Serum bactericidal responses in rhesus macaques immunized with novel vaccines containing recombinant proteins derived from the genome of N. meningitidis.*
[142] Costantino et al. (1992) *Vaccine* 10:691-698.
[143] WO03/007985.
[144] Watson (2000) *Pediatr Infect Dis J* 19:331-332.
[145] Rubin (2000) *Pediatr Clin North Am* 47:269-285, v.
[146] Jedrzejas (2001) *Microbiol Mol Biol Rev* 65:187-207.
[147] Bell (2000) *Pediatr Infect Dis J* 19:1187-1188.
[148] Iwarson (1995) *APMIS* 103:321-326.
[149] Gerlich et al. (1990) *Vaccine* 8 Suppl:S63-68 & 79-80.
[150] Hsu et al. (1999) *Clin Liver Dis* 3:901-915.
[151] Gustafsson et al. (1996) *N. Engl. J. Med.* 334:349-355.
[152] Rappuoli et al. (1991) *TIBTECH* 9:232-238.
[153] *Vaccines* (2004) eds. Plotkin & Orenstein. ISBN 0-7216-9688-0.
[154] WO02/079243.
[155] WO02/02606.
[156] Kalman et al. (1999) *Nature Genetics* 21:385-389.
[157] Read et al. (2000) *Nucleic Acids Res* 28:1397-406.
[158] Shirai et al. (2000) *J. Infect. Dis.* 181(Suppl 3):S524-S527.
[159] WO99/27105.
[160] WO00/27994.
[161] WO00/37494.
[162] WO99/28475.
[163] Ross et al. (2001) *Vaccine* 19:4135-4142.
[164] Sutter et al. (2000) *Pediatr Clin North Am* 47:287-308.
[165] Zimmerman & Spann (1999) *Am Fam Physician* 59:113-118, 125-126.
[166] Dreesen (1997) *Vaccine* 15 Suppl:S2-6.
[167] *MMWR Morb Mortal Wkly Rep* 1998 Jan. 16;47(1):12, 19.
[168] McMichael (2000) *Vaccine* 19 Suppl 1:S101-107.
[169] Schuchat (1999) *Lancet* 353(9146):51-6.
[170] WO02/34771.
[171] Dale (1999) *Infect Dis Clin North Am* 13:227-43, viii.
[172] Ferretti et al. (2001) *PNAS USA* 98: 4658-4663.
[173] Anonymous (January 2002) *Research Disclosure*, 453077.
[174] Anderson (1983) *Infect Immun* 39(1):233-238.
[175] Anderson et al. (1985) *J Clin Invest* 76(1):52-59.
[176] EP-A-0372501.
[177] EP-A-0378881.
[178] EP-A-0427347.
[179] WO93/17712.
[180] WO94/03208.
[181] WO98/58668.
[182] EP-A-0471177.
[183] WO91/01146
[184] Falugi et al. (2001) *Eur J Immunol* 31:3816-3824.
[185] EP-A-0594610.
[186] WO00/56360.
[187] WO02/091998.
[188] Kuo et al. (1995) *Infect Immun* 63:2706-13.
[189] WO01/72337.
[190] WO00/61761.
[191] WO99/24578.
[192] WO99/36544.
[193] WO99/57280.
[194] WO00/22430.
[195] WO96/29412.
[196] Pizza et al. (2000) *Science* 287:1816-1820.
[197] WO01/64920.
[198] WO03/020756.
[199] WO2004/032958.
[200] Peak et al. (2000) *FEMS Immunol Med Microbiol* 28(4):329-34,
[201] WO99/31132.
[202] Sun et al. (2005) *Vaccine* 23(32):4136-41.
[203] WO2004/014419.
[204] *Current Protocols in Molecular Biology* (F. M. Ausubel, et al., eds., 1987) Supplement 30.
[205] Smith & Waterman (1981) *Adv. Appl. Math.* 2:482-489.
[206] Fredriksen et al. (1991) *NIPH Ann.* 14:67-79.
[207] Guthrie et al. (2004) *Infect Immun* 72:2528-37.

What is claimed is:

1. A process for preparing *Escherichia* bacterial vesicles, comprising the steps of: (i) culturing an *Escherichia* bacterium in a culture medium such that the bacterium releases vesicles into said medium; and (ii) collecting the vesicles from said medium, wherein: (a) the bacterium has a cell wall that includes peptidoglycan; and (b) the bacterium has a knockout mutation of its mltA gene.

2. The process of claim 1, wherein the bacterium also has a knockout mutation of at least one further gene.

3. The process of claim 1, wherein the *Escherichia* bacterium is a pathogenic *Escherichia coli* (*E.coli*) bacterium.

4. The process of claim 3, wherein the pathogenic *E.coli* is an extraintestinal pathogenic bacterium, a uropathogenic bacterium, or a meningitis/sepsis-associated bacterium.

5. The process of claim 2, wherein the bacterium is *E.coli*.

6. The process of claim 5, wherein the bacterium is a pathogenic *E.coli*.

7. The process of claim 6, wherein the pathogenic *E.coli* is an extraintestinal pathogenic bacterium, a uropathogenic bacterium, or a meningitis/sepsis-associated bacterium.

8. The process of claim 1, wherein the bacterium is a pathogenic *Escherichia coli* bacterium, which does not express a protein of the Tol-Pal complex.

9. The process of claim 8, wherein the *E.coli* bacterium is a tolR-strain.

\* \* \* \* \*

SEQUENCE LISTING

<160> NUMBER OF SEQ ID NOS: 11

<210> SEQ ID NO 1
<211> LENGTH: 441
<212> TYPE: PRT
<213> ORGANISM: Neisseria meningitidis

<400> SEQUENCE: 1

Met Lys Lys Tyr Leu Phe Arg Ala Ala Leu Tyr Gly Ile Ala Ala Ala
1               5                   10                  15

Ile Leu Ala Ala Cys Gln Ser Lys Ser Ile Gln Thr Phe Pro Gln Pro
            20                  25                  30

Asp Thr Ser Val Ile Asn Gly Pro Asp Arg Pro Val Gly Ile Pro Asp
        35                  40                  45

Pro Ala Gly Thr Thr Val Gly Gly Gly Ala Val Tyr Thr Val Val
    50                  55                  60

Pro His Leu Ser Leu Pro His Trp Ala Ala Gln Asp Phe Ala Lys Ser
65                  70                  75                  80

Leu Gln Ser Phe Arg Leu Gly Cys Ala Asn Leu Lys Asn Arg Gln Gly
                85                  90                  95

Trp Gln Asp Val Cys Ala Gln Ala Phe Gln Thr Pro Val His Ser Phe
            100                 105                 110

Gln Ala Lys Gln Phe Phe Glu Arg Tyr Phe Thr Pro Trp Gln Val Ala
        115                 120                 125

Gly Asn Gly Ser Leu Ala Gly Thr Val Thr Gly Tyr Tyr Glu Pro Val
    130                 135                 140

Leu Lys Gly Asp Asp Arg Arg Thr Ala Gln Ala Arg Phe Pro Ile Tyr
145                 150                 155                 160

Gly Ile Pro Asp Asp Phe Ile Ser Val Pro Leu Pro Ala Gly Leu Arg
                165                 170                 175

Ser Gly Lys Ala Leu Val Arg Ile Arg Gln Thr Gly Lys Asn Ser Gly
            180                 185                 190

Thr Ile Asp Asn Thr Gly Gly Thr His Thr Ala Asp Leu Ser Arg Phe
        195                 200                 205

Pro Ile Thr Ala Arg Thr Thr Ala Ile Lys Gly Arg Phe Glu Gly Ser
    210                 215                 220

Arg Phe Leu Pro Tyr His Thr Arg Asn Gln Ile Asn Gly Gly Ala Leu
225                 230                 235                 240

Asp Gly Lys Ala Pro Ile Leu Gly Tyr Ala Glu Asp Pro Val Glu Leu
                245                 250                 255

Phe Phe Met His Ile Gln Gly Ser Gly Arg Leu Lys Thr Pro Ser Gly
            260                 265                 270

Lys Tyr Ile Arg Ile Gly Tyr Ala Asp Lys Asn Glu His Pro Tyr Val
        275                 280                 285

Ser Ile Gly Arg Tyr Met Ala Asp Lys Gly Tyr Leu Lys Leu Gly Gln
    290                 295                 300

Thr Ser Met Gln Gly Ile Lys Ser Tyr Met Arg Gln Asn Pro Gln Arg
305                 310                 315                 320

Leu Ala Glu Val Leu Gly Gln Asn Pro Ser Tyr Ile Phe Phe Arg Glu
                325                 330                 335

Leu Ala Gly Ser Ser Asn Asp Gly Pro Val Gly Ala Leu Gly Thr Pro
            340                 345                 350

Leu Met Gly Glu Tyr Ala Gly Ala Val Asp Arg His Tyr Ile Thr Leu
        355                 360                 365

Gly Ala Pro Leu Phe Val Ala Thr Ala His Pro Val Thr Arg Lys Ala
    370                 375                 380

Leu Asn Arg Leu Ile Met Ala Gln Asp Thr Gly Ser Ala Ile Lys Gly
385                 390                 395                 400

Ala Val Arg Val Asp Tyr Phe Trp Gly Tyr Gly Asp Glu Ala Gly Glu
                405                 410                 415

Leu Ala Gly Lys Gln Lys Thr Thr Gly Tyr Val Trp Gln Leu Leu Pro
            420                 425                 430

Asn Gly Met Lys Pro Glu Tyr Arg Pro
            435                 440

<210> SEQ ID NO 2
<211> LENGTH: 1326
<212> TYPE: DNA
<213> ORGANISM: Neisseria meningitidis

<400> SEQUENCE: 2

| | | | | | |
|---|---|---|---|---|---|
| atgaaaaaat | acctattccg | cgccgccctg | tacggcatcg | ccgccgccat | cctcgccgcc | 60 |
| tgccaaagca | agagcatcca | aacctttccg | caacccgaca | catccgtcat | caacggcccg | 120 |
| gaccggccgg | tcggcatccc | cgaccccgcc | ggaacgacgg | tcggcggcgg | cggggccgtc | 180 |
| tataccgttg | taccgcacct | gtccctgccc | cactgggcgg | cgcaggattt | cgccaaaagc | 240 |
| ctgcaatcct | tccgcctcgg | ctgcgccaat | ttgaaaaacc | gccaaggctg | caggatgtg | 300 |
| tgcgcccaag | cctttcaaac | ccccgtccat | tcctttcagg | caaaacagtt | ttttgaacgc | 360 |
| tatttcacgc | cgtggcaggt | tgcaggcaac | ggaagccttg | ccggtacggt | taccggctat | 420 |
| tacgaaccgg | tgctgaaggg | cgacgacagg | cggacggcac | aagcccgctt | cccgatttac | 480 |
| ggtattcccg | acgattttat | ctccgtcccc | ctgcctgccg | gtttgcggag | cggaaaagcc | 540 |
| cttgtccgca | tcaggcagac | gggaaaaaac | agcggcacaa | tcgacaatac | cggcggcaca | 600 |
| cataccgccg | acctctcccg | attccccatc | accgcgcgca | aacagcaat | caaaggcagg | 660 |
| tttgaaggaa | gccgcttcct | cccctaccac | acgcgcaacc | aaatcaacgg | cggcgcgctt | 720 |
| gacggcaaag | ccccgatact | cggttacgcc | gaagaccctg | tcgaactttt | ttttatgcac | 780 |
| atccaaggct | cgggccgtct | gaaaaccccg | tccggcaaat | acatccgcat | cggctatgcc | 840 |
| gacaaaaacg | aacatcccta | cgtttccatc | ggacgctata | tggcggataa | gggctacctc | 900 |
| aaactcggac | aaacctccat | gcagggcatt | aagtcttata | tgcggcaaaa | tccgcaacgc | 960 |
| ctcgccgaag | tttgggtca | aaaccccagc | tatatctttt | tccgcgagct | tgccggaagc | 1020 |
| agcaatgacg | gccctgtcgg | cgcactgggc | acgccgctga | tggggaata | tgccggcgca | 1080 |
| gtcgaccggc | actacattac | cttgggtgcg | cccttatttg | tcgccaccgc | ccatccggtt | 1140 |
| acccgcaaag | ccctcaaccg | cctgattatg | gcgcaggata | ccggcagcgc | gattaaaggc | 1200 |
| gcggtgcgcg | tggattattt | ttggggatac | ggcgacgaag | ccggcgaact | tgccggcaaa | 1260 |
| cagaaaacca | cgggatatgt | ctggcagctc | ctacccaacg | gtatgaagcc | cgaataccgc | 1320 |
| ccgtaa | | | | | | 1326 |

<210> SEQ ID NO 3
<211> LENGTH: 398
<212> TYPE: PRT
<213> ORGANISM: Neisseria meningitidis

```
<400> SEQUENCE: 3

Met Pro Ser Glu Pro Phe Gly Arg His Asn Ala Thr Asn Thr Leu Ile
1               5                   10                  15

Ser Ile Thr Gln Asp Asp Thr Met Thr His Ile Lys Pro Val Ile Ala
            20                  25                  30

Ala Leu Ala Leu Ile Gly Leu Ala Ala Cys Ser Gly Ser Lys Thr Glu
        35                  40                  45

Gln Pro Lys Leu Asp Tyr Gln Ser Arg Ser His Arg Leu Ile Lys Leu
    50                  55                  60

Glu Val Pro Pro Asp Leu Asn Asn Pro Asp Gln Gly Asn Leu Tyr Arg
65                  70                  75                  80

Leu Pro Ala Gly Ser Gly Ala Val Arg Ala Ser Asp Leu Glu Lys Arg
                85                  90                  95

Arg Thr Pro Ala Val Gln Gln Pro Ala Asp Ala Glu Val Leu Lys Ser
            100                 105                 110

Val Lys Gly Val Arg Leu Glu Arg Asp Gly Ser Gln Arg Trp Leu Val
        115                 120                 125

Val Asp Gly Lys Ser Pro Ala Glu Ile Trp Pro Leu Leu Lys Ala Phe
    130                 135                 140

Trp Gln Glu Asn Gly Phe Asp Ile Lys Ser Glu Glu Pro Ala Ile Gly
145                 150                 155                 160

Gln Met Glu Thr Glu Trp Ala Glu Asn Arg Ala Lys Ile Pro Gln Asp
                165                 170                 175

Ser Leu Arg Arg Leu Phe Asp Lys Val Gly Leu Gly Gly Ile Tyr Ser
            180                 185                 190

Thr Gly Glu Arg Asp Lys Phe Ile Val Arg Ile Glu Gln Gly Lys Asn
        195                 200                 205

Gly Val Ser Asp Ile Phe Phe Ala His Lys Ala Met Lys Glu Val Tyr
    210                 215                 220

Gly Gly Lys Asp Lys Asp Thr Thr Val Trp Gln Pro Ser Pro Ser Asp
225                 230                 235                 240

Pro Asn Leu Glu Ala Ala Phe Leu Thr Arg Phe Met Gln Tyr Leu Gly
                245                 250                 255

Val Asp Gly Gln Gln Ala Glu Asn Ala Ser Lys Lys Pro Thr Leu
            260                 265                 270

Pro Ala Ala Asn Glu Met Ala Arg Ile Glu Gly Lys Ser Leu Ile Val
        275                 280                 285

Phe Gly Asp Tyr Gly Arg Asn Trp Arg Arg Thr Val Leu Ala Leu Asp
    290                 295                 300

Arg Ile Gly Leu Thr Val Val Gly Gln Asn Thr Glu Arg His Ala Phe
305                 310                 315                 320

Leu Val Gln Lys Ala Pro Asn Glu Ser Asn Ala Val Thr Glu Gln Lys
                325                 330                 335

Pro Gly Leu Phe Lys Arg Leu Leu Gly Lys Gly Lys Ala Glu Lys Pro
            340                 345                 350

Ala Glu Gln Pro Glu Leu Ile Val Tyr Ala Glu Pro Val Ala Asn Gly
        355                 360                 365

Ser Arg Ile Val Leu Leu Asn Lys Asp Gly Ser Ala Tyr Ala Gly Lys
    370                 375                 380

Asp Ala Ser Ala Leu Leu Gly Lys Leu His Ser Glu Leu Arg
385                 390                 395
```

```
<210> SEQ ID NO 4
<211> LENGTH: 443
<212> TYPE: PRT
<213> ORGANISM: Neisseria meningitidis

<400> SEQUENCE: 4

Met Leu Lys Cys Gly Thr Phe Phe Ile Thr Arg His Ile Pro Arg Gly
1               5                   10                  15

Cys Arg Arg Phe Phe Gln Pro Asn Gln Ala Arg Gln Thr Glu Ile Tyr
            20                  25                  30

Gln Ile Arg Gly Thr Val Met Gln Arg Arg Ile Ile Thr Leu Leu Cys
        35                  40                  45

Ala Ala Gly Met Ala Phe Ser Thr Gln Thr Leu Ala Ala Asn Leu Glu
    50                  55                  60

Val Arg Pro Asn Ala Pro Glu Arg Tyr Thr Val Lys Gln Gly Asp Thr
65                  70                  75                  80

Leu Trp Gly Ile Ser Gly Lys Tyr Leu Tyr Ser Pro Trp Gln Trp Gly
                85                  90                  95

Arg Leu Trp Asp Ala Asn Arg Asp Gln Ile His Asn Pro Asp Leu Ile
            100                 105                 110

Tyr Pro Asp Gln Val Leu Val Leu Arg His Val Asp Gly Glu Pro Arg
        115                 120                 125

Leu Gly Leu Glu Gln Thr Asp Gly Ile Pro Val Val Lys Met Ser Pro
    130                 135                 140

Asp Lys Glu Val Ser Gly Tyr Gly Ile Pro Ala Ile Asp Val Asn Phe
145                 150                 155                 160

Tyr Arg Ile Phe Met Arg His Pro Gln Ile Val Ser Arg Lys Glu Thr
                165                 170                 175

Ala Ala Ala Pro Arg Leu Leu Ser Gly Pro Glu Gly Arg Leu Leu Tyr
            180                 185                 190

Thr Lys Gly Thr Arg Val Tyr Thr Lys Gly Leu Lys Glu Pro Gly Arg
        195                 200                 205

Tyr Leu Thr Tyr Arg Ile Asn Lys Asn Ile Thr Asp Pro Asp Thr Gly
    210                 215                 220

Lys Phe Leu Gly Gln Glu Val Ala Phe Ser Gly Ile Val Arg Ser Leu
225                 230                 235                 240

Asp Tyr Thr Asp Ser Val Leu Glu Gln Arg Ser Lys Gln Ala Gly Glu
                245                 250                 255

Arg Pro Lys Asp Asn Glu Tyr His Thr Arg Thr His Pro Leu Ile Thr
            260                 265                 270

Pro Leu Arg Thr Pro Ser Ile Gln Pro Leu Val Val Glu Thr Ala Ile
        275                 280                 285

Ser Glu Ile Gln Gln Gly Asp Tyr Leu Met Lys Met Pro Glu Asp Thr
    290                 295                 300

Asp Arg Phe Asn Met Met Pro His Glu Pro Ser Arg Pro Val Gln Ala
305                 310                 315                 320

Lys Ile Val Ser Val Phe Glu Gly Thr Arg Ile Ala Gly Gln Phe Gln
                325                 330                 335

Thr Ile Thr Ile Asp Lys Gly Glu Ala Asp Gly Leu Asp Lys Gly Thr
            340                 345                 350

Val Leu Ser Leu Tyr Lys Arg Lys Thr Met Gln Val Asp Leu Ser
        355                 360                 365

Asn Asn Phe Lys Ser Arg Asp Thr Val Glu Leu Ile Ser Thr Pro Ala
    370                 375                 380
```

-continued

```
Glu Glu Val Gly Leu Ala Met Val Tyr Arg Thr Ser Glu His Leu Ser
385                 390                 395                 400

Ser Ala Ile Ile Leu Glu Asn Ile Ser Asp Ile Ser Val Gly Asp Thr
            405                 410                 415

Ala Ala Asn Pro Gly Arg Asp Leu Asp Asn Ile Pro Asp Gln Gly Arg
        420                 425                 430

Ser Arg Val Lys Phe Gly Phe Asn Arg Ser Glu
    435                 440

<210> SEQ ID NO 5
<211> LENGTH: 606
<212> TYPE: PRT
<213> ORGANISM: Neisseria meningitidis

<400> SEQUENCE: 5

Met Pro Cys Met Asn His Gln Ser Asn Ser Gly Glu Gly Val Leu Val
1               5                   10                  15

Ala Lys Thr Tyr Leu Leu Thr Ala Leu Ile Met Ser Met Thr Ile Ser
            20                  25                  30

Gly Cys Gln Val Ile His Ala Asn Gln Gly Lys Val Asn Thr His Ser
        35                  40                  45

Ala Val Ile Thr Gly Ala Asp Ala His Thr Pro Glu His Ala Thr Gly
    50                  55                  60

Leu Thr Glu Gln Lys Gln Val Ile Ala Ser Asp Phe Met Val Ala Ser
65                  70                  75                  80

Ala Asn Pro Leu Ala Thr Gln Ala Gly Tyr Asp Ile Leu Lys Gln Gly
                85                  90                  95

Gly Ser Ala Ala Asp Ala Met Val Ala Val Gln Thr Thr Leu Ser Leu
            100                 105                 110

Val Glu Pro Gln Ser Ser Gly Leu Gly Gly Gly Ala Phe Val Leu Tyr
        115                 120                 125

Trp Asp Asn Thr Ala Lys Thr Leu Thr Thr Phe Asp Gly Arg Glu Thr
    130                 135                 140

Ala Pro Met Arg Ala Thr Pro Glu Leu Phe Leu Asp Lys Asp Gly Gln
145                 150                 155                 160

Pro Leu Lys Phe Met Glu Ala Val Val Gly Gly Arg Ser Val Gly Thr
                165                 170                 175

Pro Ala Ile Pro Lys Leu Met Glu Thr Ile His Gln Arg Tyr Gly Val
            180                 185                 190

Leu Pro Trp Gly Lys Leu Phe Asp Thr Pro Ile Arg Leu Ala Lys Gln
        195                 200                 205

Gly Phe Glu Val Ser Pro Arg Leu Ala Ile Ser Val Glu Gln Asn Gln
    210                 215                 220

Gln His Leu Ala Arg Tyr Pro Lys Thr Ala Ala Tyr Phe Leu Pro Asn
225                 230                 235                 240

Gly Val Pro Leu Gln Ala Gly Ser Leu Leu Lys Asn Leu Glu Phe Ala
                245                 250                 255

Asp Ser Val Gln Ala Leu Ala Ala Gln Gly Ala Lys Ala Leu His Thr
            260                 265                 270

Gly Lys Tyr Ala Gln Asn Ile Val Ser Val Gln Asn Ala Lys Asp
        275                 280                 285

Asn Pro Gly Gln Leu Ser Leu Gln Asp Leu Ser Asp Tyr Gln Val Val
    290                 295                 300

Glu Arg Pro Pro Val Cys Val Thr Tyr Arg Ile Tyr Glu Val Cys Gly
305                 310                 315                 320
```

Met Gly Ala Pro Ser Ser Gly Gly Ile Ala Val Gly Gln Ile Leu Gly
                325                 330                 335

Ile Leu Asn Glu Phe Ser Pro Asn Gln Val Gly Tyr Asp Ala Glu Gly
            340                 345                 350

Leu Arg Leu Leu Gly Asp Ala Ser Arg Leu Ala Phe Ala Asp Arg Asp
        355                 360                 365

Val Tyr Leu Gly Asp Pro Asp Phe Val Pro Val Pro Ile Arg Gln Leu
    370                 375                 380

Ile Ser Lys Asp Tyr Leu Lys His Arg Ser Gln Leu Leu Glu Gln Ser
385                 390                 395                 400

Asp Lys Ala Leu Pro Ser Val Ser Ala Gly Asp Phe Ile His Glu Trp
                405                 410                 415

Val Ser Ser Gln Ala Ile Glu Leu Pro Ser Thr Ser His Ile Ser Ile
            420                 425                 430

Val Asp Lys Ala Gly Asn Val Leu Ser Met Thr Thr Ser Ile Glu Asn
        435                 440                 445

Ala Phe Gly Ser Thr Leu Met Ala Asn Gly Tyr Leu Leu Asn Asn Glu
    450                 455                 460

Leu Thr Asp Phe Ser Phe Glu Pro Ile Lys Gln Gly Lys Gln Val Ala
465                 470                 475                 480

Asn Arg Val Glu Pro Gly Lys Arg Pro Arg Ser Ser Met Ala Pro Thr
                485                 490                 495

Ile Val Phe Lys Ala Gly Lys Pro Tyr Met Ala Ile Gly Ser Pro Gly
            500                 505                 510

Gly Ser Arg Ile Ile Gly Tyr Val Ala Lys Thr Ile Val Ala His Ser
        515                 520                 525

Asp Trp Asn Met Asp Ile Gln Asn Ala Ile Ser Ala Pro Asn Leu Leu
    530                 535                 540

Asn Arg Phe Gly Ser Tyr Glu Leu Glu Thr Gly Thr Thr Ala Val Gln
545                 550                 555                 560

Trp Gln Gln Ala Leu Asn Asp Leu Gly Tyr Lys Thr Asp Val Arg Glu
                565                 570                 575

Leu Asn Ser Gly Val Gln Ala Ile Ile Ile Glu Pro Ser Arg Leu Val
            580                 585                 590

Gly Gly Ala Asp Pro Arg Arg Glu Gly Arg Val Met Gly Asp
        595                 600                 605

<210> SEQ ID NO 6
<211> LENGTH: 375
<212> TYPE: PRT
<213> ORGANISM: Neisseria meningitidis

<400> SEQUENCE: 6

Met Thr His Ile Lys Pro Val Ile Ala Ala Leu Ala Leu Ile Gly Leu
1               5                   10                  15

Ala Ala Cys Ser Gly Ser Lys Thr Glu Gln Pro Lys Leu Asp Tyr Gln
                20                  25                  30

Ser Arg Ser His Arg Leu Ile Lys Leu Glu Val Pro Pro Asp Leu Asn
            35                  40                  45

Asn Pro Asp Gln Gly Asn Leu Tyr Arg Leu Pro Ala Gly Ser Gly Ala
        50                  55                  60

Val Arg Ala Ser Asp Leu Glu Lys Arg Thr Pro Ala Val Gln Gln
65                  70                  75                  80

Pro Ala Asp Ala Glu Val Leu Lys Ser Val Lys Gly Val Arg Leu Glu
                85                  90                  95

Arg Asp Gly Ser Gln Arg Trp Leu Val Val Asp Gly Lys Ser Pro Ala
            100                 105                 110

Glu Ile Trp Pro Leu Leu Lys Ala Phe Trp Gln Glu Asn Gly Phe Asp
        115                 120                 125

Ile Lys Ser Glu Glu Pro Ala Ile Gly Gln Met Glu Thr Glu Trp Ala
        130                 135                 140

Glu Asn Arg Ala Lys Ile Pro Gln Asp Ser Leu Arg Arg Leu Phe Asp
145                 150                 155                 160

Lys Val Gly Leu Gly Gly Ile Tyr Ser Thr Gly Glu Arg Asp Lys Phe
                165                 170                 175

Ile Val Arg Ile Glu Gln Gly Lys Asn Gly Val Ser Asp Ile Phe Phe
            180                 185                 190

Ala His Lys Ala Met Lys Glu Val Tyr Gly Gly Lys Asp Lys Asp Thr
        195                 200                 205

Thr Val Trp Gln Pro Ser Pro Ser Asp Pro Asn Leu Glu Ala Ala Phe
        210                 215                 220

Leu Thr Arg Phe Met Gln Tyr Leu Gly Val Asp Gly Gln Gln Ala Glu
225                 230                 235                 240

Asn Ala Ser Ala Lys Lys Pro Thr Leu Pro Ala Ala Asn Glu Met Ala
                245                 250                 255

Arg Ile Glu Gly Lys Ser Leu Ile Val Phe Gly Asp Tyr Gly Arg Asn
            260                 265                 270

Trp Arg Arg Thr Val Leu Ala Leu Asp Arg Ile Gly Leu Thr Val Val
        275                 280                 285

Gly Gln Asn Thr Glu Arg His Ala Phe Leu Val Gln Lys Ala Pro Asn
        290                 295                 300

Glu Ser Asn Ala Val Thr Glu Gln Lys Pro Gly Leu Phe Lys Arg Leu
305                 310                 315                 320

Leu Gly Lys Gly Lys Ala Glu Lys Pro Ala Glu Gln Pro Glu Leu Ile
                325                 330                 335

Val Tyr Ala Glu Pro Val Ala Asn Gly Ser Arg Ile Val Leu Leu Asn
            340                 345                 350

Lys Asp Gly Ser Ala Tyr Ala Gly Lys Asp Ala Ser Ala Leu Leu Gly
        355                 360                 365

Lys Leu His Ser Glu Leu Arg
        370                 375

<210> SEQ ID NO 7
<211> LENGTH: 405
<212> TYPE: PRT
<213> ORGANISM: Neisseria meningitidis

<400> SEQUENCE: 7

Met Gln Arg Arg Ile Ile Thr Leu Leu Cys Ala Ala Gly Met Ala Phe
1               5                   10                  15

Ser Thr Gln Thr Leu Ala Ala Asn Leu Glu Val Arg Pro Asn Ala Pro
            20                  25                  30

Glu Arg Tyr Thr Val Lys Gln Gly Asp Thr Leu Trp Gly Ile Ser Gly
        35                  40                  45

Lys Tyr Leu Tyr Ser Pro Trp Gln Trp Gly Arg Leu Trp Asp Ala Asn
    50                  55                  60

Arg Asp Gln Ile His Asn Pro Asp Leu Ile Tyr Pro Asp Gln Val Leu
65                  70                  75                  80

Val Leu Arg His Val Asp Gly Glu Pro Arg Leu Gly Leu Glu Gln Thr
                85                  90                  95

```
Asp Gly Ile Pro Val Val Lys Met Ser Pro Asp Lys Glu Val Ser Gly
                100                 105                 110

Tyr Gly Ile Pro Ala Ile Asp Val Asn Phe Tyr Arg Ile Phe Met Arg
            115                 120                 125

His Pro Gln Ile Val Ser Arg Lys Glu Thr Ala Ala Pro Arg Leu
        130                 135                 140

Leu Ser Gly Pro Glu Gly Arg Leu Leu Tyr Thr Lys Gly Thr Arg Val
145                 150                 155                 160

Tyr Thr Lys Gly Leu Lys Glu Pro Gly Arg Tyr Leu Thr Tyr Arg Ile
                165                 170                 175

Asn Lys Asn Ile Thr Asp Pro Asp Thr Gly Lys Phe Leu Gly Gln Glu
            180                 185                 190

Val Ala Phe Ser Gly Ile Val Arg Ser Leu Asp Tyr Thr Asp Ser Val
        195                 200                 205

Leu Glu Gln Arg Ser Lys Gln Ala Gly Glu Arg Pro Lys Asp Asn Glu
210                 215                 220

Tyr His Thr Arg Thr His Pro Leu Ile Thr Pro Leu Arg Thr Pro Ser
225                 230                 235                 240

Ile Gln Pro Leu Val Val Glu Thr Ala Ile Ser Glu Ile Gln Gln Gly
                245                 250                 255

Asp Tyr Leu Met Lys Met Pro Glu Asp Thr Asp Arg Phe Asn Met Met
            260                 265                 270

Pro His Glu Pro Ser Arg Pro Val Gln Ala Lys Ile Val Ser Val Phe
        275                 280                 285

Glu Gly Thr Arg Ile Ala Gly Gln Phe Gln Thr Ile Thr Ile Asp Lys
290                 295                 300

Gly Glu Ala Asp Gly Leu Asp Lys Gly Thr Val Leu Ser Leu Tyr Lys
305                 310                 315                 320

Arg Lys Lys Thr Met Gln Val Asp Leu Ser Asn Asn Phe Lys Ser Arg
                325                 330                 335

Asp Thr Val Glu Leu Ile Ser Thr Pro Ala Glu Glu Val Gly Leu Ala
            340                 345                 350

Met Val Tyr Arg Thr Ser Glu His Leu Ser Ser Ala Ile Ile Leu Glu
        355                 360                 365

Asn Ile Ser Asp Ile Ser Val Gly Asp Thr Ala Ala Asn Pro Gly Arg
370                 375                 380

Asp Leu Asp Asn Ile Pro Asp Gln Gly Arg Ser Arg Val Lys Phe Gly
385                 390                 395                 400

Phe Asn Arg Ser Glu
                405

<210> SEQ ID NO 8
<211> LENGTH: 593
<212> TYPE: PRT
<213> ORGANISM: Neisseria meningitidis

<400> SEQUENCE: 8

Met Leu Val Ala Lys Thr Tyr Leu Leu Thr Ala Leu Ile Met Ser Met
1               5                   10                  15

Thr Ile Ser Gly Cys Gln Val Ile His Ala Asn Gln Gly Lys Val Asn
            20                  25                  30

Thr His Ser Ala Val Ile Thr Gly Ala Asp Ala His Thr Pro Glu His
        35                  40                  45

Ala Thr Gly Leu Thr Glu Gln Lys Gln Val Ile Ala Ser Asp Phe Met
    50                  55                  60
```

```
Val Ala Ser Ala Asn Pro Leu Ala Thr Gln Ala Gly Tyr Asp Ile Leu
 65                  70                  75                  80

Lys Gln Gly Gly Ser Ala Ala Asp Ala Met Val Ala Val Gln Thr Thr
                 85                  90                  95

Leu Ser Leu Val Glu Pro Gln Ser Ser Gly Leu Gly Gly Gly Ala Phe
            100                 105                 110

Val Leu Tyr Trp Asp Asn Thr Ala Lys Thr Leu Thr Thr Phe Asp Gly
        115                 120                 125

Arg Glu Thr Ala Pro Met Arg Ala Thr Pro Glu Leu Phe Leu Asp Lys
    130                 135                 140

Asp Gly Gln Pro Leu Lys Phe Met Glu Ala Val Val Gly Gly Arg Ser
145                 150                 155                 160

Val Gly Thr Pro Ala Ile Pro Lys Leu Met Glu Thr Ile His Gln Arg
                165                 170                 175

Tyr Gly Val Leu Pro Trp Gly Lys Leu Phe Asp Thr Pro Ile Arg Leu
            180                 185                 190

Ala Lys Gln Gly Phe Glu Val Ser Pro Arg Leu Ala Ile Ser Val Glu
        195                 200                 205

Gln Asn Gln Gln His Leu Ala Arg Tyr Pro Lys Thr Ala Ala Tyr Phe
    210                 215                 220

Leu Pro Asn Gly Val Pro Leu Gln Ala Gly Ser Leu Leu Lys Asn Leu
225                 230                 235                 240

Glu Phe Ala Asp Ser Val Gln Ala Leu Ala Ala Gln Gly Ala Lys Ala
                245                 250                 255

Leu His Thr Gly Lys Tyr Ala Gln Asn Ile Val Ser Val Val Gln Asn
            260                 265                 270

Ala Lys Asp Asn Pro Gly Gln Leu Ser Leu Gln Asp Leu Ser Asp Tyr
        275                 280                 285

Gln Val Val Glu Arg Pro Pro Val Cys Val Thr Tyr Arg Ile Tyr Glu
    290                 295                 300

Val Cys Gly Met Gly Ala Pro Ser Ser Gly Gly Ile Ala Val Gly Gln
305                 310                 315                 320

Ile Leu Gly Ile Leu Asn Glu Phe Ser Pro Asn Gln Val Gly Tyr Asp
                325                 330                 335

Ala Glu Gly Leu Arg Leu Leu Gly Asp Ala Ser Arg Leu Ala Phe Ala
            340                 345                 350

Asp Arg Asp Val Tyr Leu Gly Asp Pro Asp Phe Val Pro Val Pro Ile
        355                 360                 365

Arg Gln Leu Ile Ser Lys Asp Tyr Leu Lys His Arg Ser Gln Leu Leu
    370                 375                 380

Glu Gln Ser Asp Lys Ala Leu Pro Ser Val Ser Ala Gly Asp Phe Ile
385                 390                 395                 400

His Glu Trp Val Ser Ser Gln Ala Ile Glu Leu Pro Ser Thr Ser His
                405                 410                 415

Ile Ser Ile Val Asp Lys Ala Gly Asn Val Leu Ser Met Thr Thr Ser
            420                 425                 430

Ile Glu Asn Ala Phe Gly Ser Thr Leu Met Ala Asn Gly Tyr Leu Leu
        435                 440                 445

Asn Asn Glu Leu Thr Asp Phe Ser Phe Glu Pro Ile Lys Gln Gly Lys
    450                 455                 460

Gln Val Ala Asn Arg Val Glu Pro Gly Lys Arg Pro Arg Ser Ser Met
465                 470                 475                 480
```

-continued

```
Ala Pro Thr Ile Val Phe Lys Ala Gly Lys Pro Tyr Met Ala Ile Gly
                485                 490                 495

Ser Pro Gly Gly Ser Arg Ile Ile Gly Tyr Val Ala Lys Thr Ile Val
            500                 505                 510

Ala His Ser Asp Trp Asn Met Asp Ile Gln Asn Ala Ile Ser Ala Pro
            515                 520                 525

Asn Leu Leu Asn Arg Phe Gly Ser Tyr Glu Leu Glu Thr Gly Thr Thr
        530                 535                 540

Ala Val Gln Trp Gln Gln Ala Leu Asn Asp Leu Gly Tyr Lys Thr Asp
545                 550                 555                 560

Val Arg Glu Leu Asn Ser Gly Val Gln Ala Ile Ile Ile Glu Pro Ser
                565                 570                 575

Arg Leu Val Gly Gly Ala Asp Pro Arg Arg Glu Gly Arg Val Met Gly
            580                 585                 590

Asp

<210> SEQ ID NO 9
<211> LENGTH: 18
<212> TYPE: PRT
<213> ORGANISM: Neisseria meningitidis

<400> SEQUENCE: 9

Met Thr His Ile Lys Pro Val Ile Ala Ala Leu Ala Leu Ile Gly Leu
1               5                   10                  15

Ala Ala

<210> SEQ ID NO 10
<211> LENGTH: 38
<212> TYPE: PRT
<213> ORGANISM: Neisseria meningitidis

<400> SEQUENCE: 10

Met Leu Lys Cys Gly Thr Phe Phe Ile Thr Arg His Ile Pro Arg Gly
1               5                   10                  15

Cys Arg Arg Phe Phe Gln Pro Asn Gln Ala Arg Gln Thr Glu Ile Tyr
            20                  25                  30

Gln Ile Arg Gly Thr Val
        35

<210> SEQ ID NO 11
<211> LENGTH: 10
<212> TYPE: PRT
<213> ORGANISM: Neisseria meningitidis

<400> SEQUENCE: 11

Met Pro Cys Met Asn His Gln Ser Asn Ser
1               5                   10
```